US012653611B2

(12) United States Patent
Gliner et al.

(10) Patent No.: US 12,653,611 B2
(45) Date of Patent: Jun. 16, 2026

(54) SYSTEMS AND METHODS OF POSITION SENSING

(71) Applicant: BIOSENSE WEBSTER (ISRAEL) LTD., Yokneam (IL)

(72) Inventors: Vadim Gliner, Haifa (IL); Uri Avni, Ram-Om (IL); Alon Boumendil, Haifa (IL); Amit Fuchs, Hogla (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 171 days.

(21) Appl. No.: 18/827,988

(22) Filed: Sep. 9, 2024

(65) Prior Publication Data

US 2026/0069353 A1     Mar. 12, 2026

(51) Int. Cl.
*A61B 18/14* (2006.01)
*G16H 40/63* (2018.01)
*A61B 18/00* (2006.01)

(52) U.S. Cl.
CPC ......... *A61B 18/1492* (2013.01); *G16H 40/63* (2018.01); *A61B 2018/00267* (2013.01); *A61B 2018/00577* (2013.01); *A61B 2018/00773* (2013.01); *A61B 2018/00839* (2013.01); *A61B 2560/0238* (2013.01)

(58) Field of Classification Search
CPC ...... A61B 18/1492; A61B 2018/00267; A61B 2018/00577; A61B 2018/00773; A61B 2018/00839; A61B 2034/105; A61B 2034/2051; A61B 2090/365; A61B 2560/0238; A61B 34/20; A61B 5/062; A61B 5/287; A61B 5/367; A61B 5/6858; A61B 5/7285; G16H 40/63
See application file for complete search history.

(56) References Cited

U.S. PATENT DOCUMENTS

| | | |
|---|---|---|
| 5,391,199 A | 2/1995 | Ben Haim |
| 5,443,489 A | 8/1995 | Ben Haim |
| 5,558,091 A | 9/1996 | Acker |

(Continued)

OTHER PUBLICATIONS

Extended European Search Report, received for European Application No. 25200694.5, mailed on Oct. 31, 2025, 06 pages.

*Primary Examiner* — Michael F Peffley

(57)     ABSTRACT

Disclosed is a positioning system adapted to determine positions of medical devices/instruments from position signals acquired by at least a first and second signal acquisition devices sampling outputs from different position sensors of the medical devices and transmitting them in packets. The system includes a calibration signal generator which is connectable to each of the acquisition devices and generates a calibration signal whose frequency is switched between a plurality of frequencies. A synchronization processor processes concurrent packets including the calibration signal sampled by the first and second acquisition devices and thereby determines synchronization parameters for synchronizing between the position signals sampled by the different acquisition devices. For example, the synchronization processor is adapted to determine respective transition times between two frequencies in the calibration signal sampled by each of the acquisition devices, and based on the transition times, determine time shift(s) between the samplings made by the different acquisition devices.

19 Claims, 5 Drawing Sheets

(56)  References Cited

U.S. PATENT DOCUMENTS

| | | | |
|---|---|---|---|
| 6,172,499 B1 | 1/2001 | Ashe | |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |
| 6,788,967 B2 | 9/2004 | Ben Haim | |
| 6,892,091 B1 | 5/2005 | Ben Haim | |
| 7,729,742 B2 * | 6/2010 | Govari | A61B 5/0031 |
| | | | 600/133 |
| 8,494,613 B2 * | 7/2013 | Markowitz | A61B 90/13 |
| | | | 600/117 |
| 9,241,632 B2 * | 1/2016 | Kilim | A61B 5/0006 |
| 10,874,462 B2 * | 12/2020 | Govari | A61B 34/20 |
| 2011/0054304 A1 | 3/2011 | Markowitz et al. | |
| 2013/0023746 A1 | 1/2013 | Kilim et al. | |

* cited by examiner

200 - A method to determine positions of medical devices or portions thereof

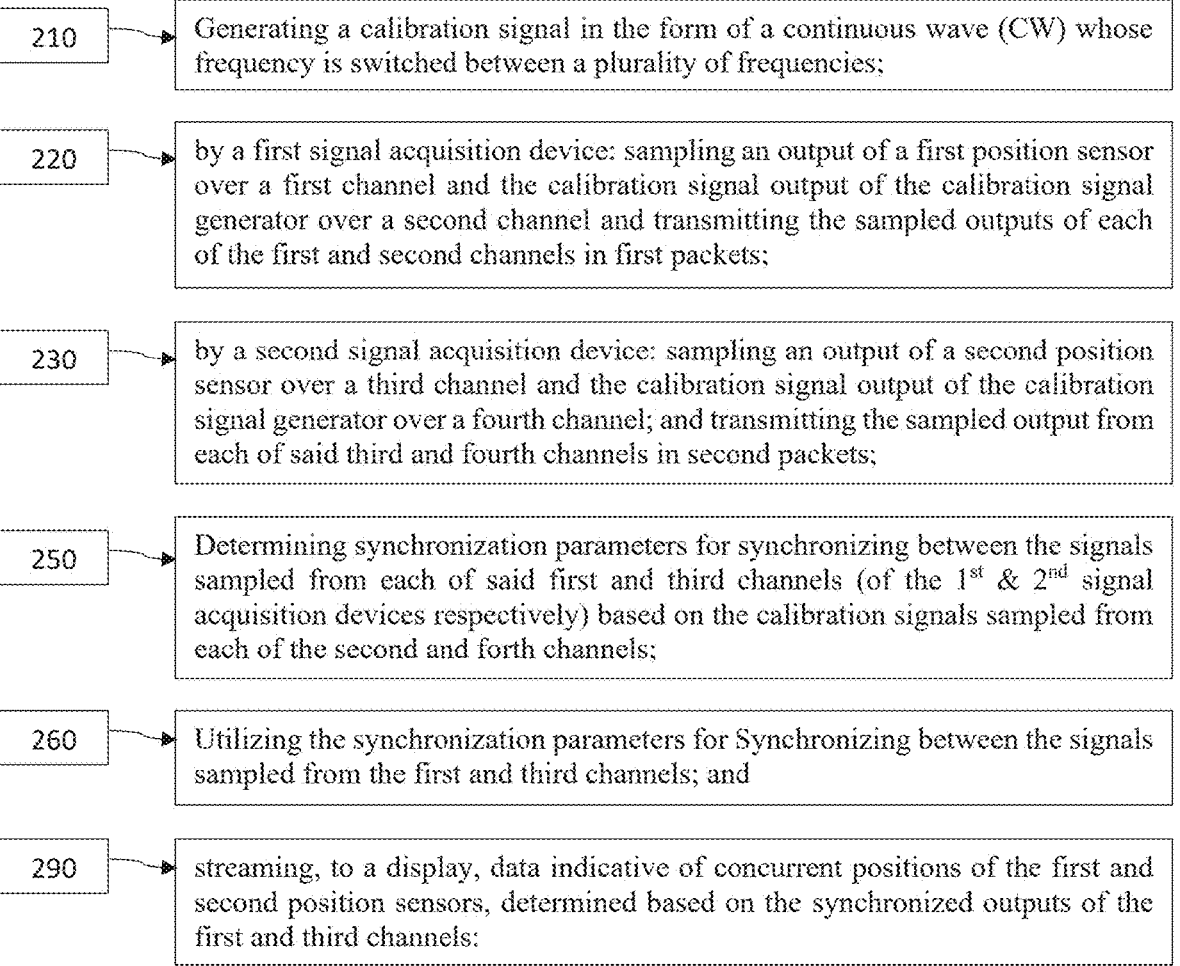

| 210 | Generating a calibration signal in the form of a continuous wave (CW) whose frequency is switched between a plurality of frequencies; |

| 220 | by a first signal acquisition device: sampling an output of a first position sensor over a first channel and the calibration signal output of the calibration signal generator over a second channel and transmitting the sampled outputs of each of the first and second channels in first packets; |

| 230 | by a second signal acquisition device: sampling an output of a second position sensor over a third channel and the calibration signal output of the calibration signal generator over a fourth channel; and transmitting the sampled output from each of said third and fourth channels in second packets; |

| 250 | Determining synchronization parameters for synchronizing between the signals sampled from each of said first and third channels (of the $1^{st}$ & $2^{nd}$ signal acquisition devices respectively) based on the calibration signals sampled from each of the second and forth channels; |

| 260 | Utilizing the synchronization parameters for Synchronizing between the signals sampled from the first and third channels; and |

| 290 | streaming, to a display, data indicative of concurrent positions of the first and second position sensors, determined based on the synchronized outputs of the first and third channels; |

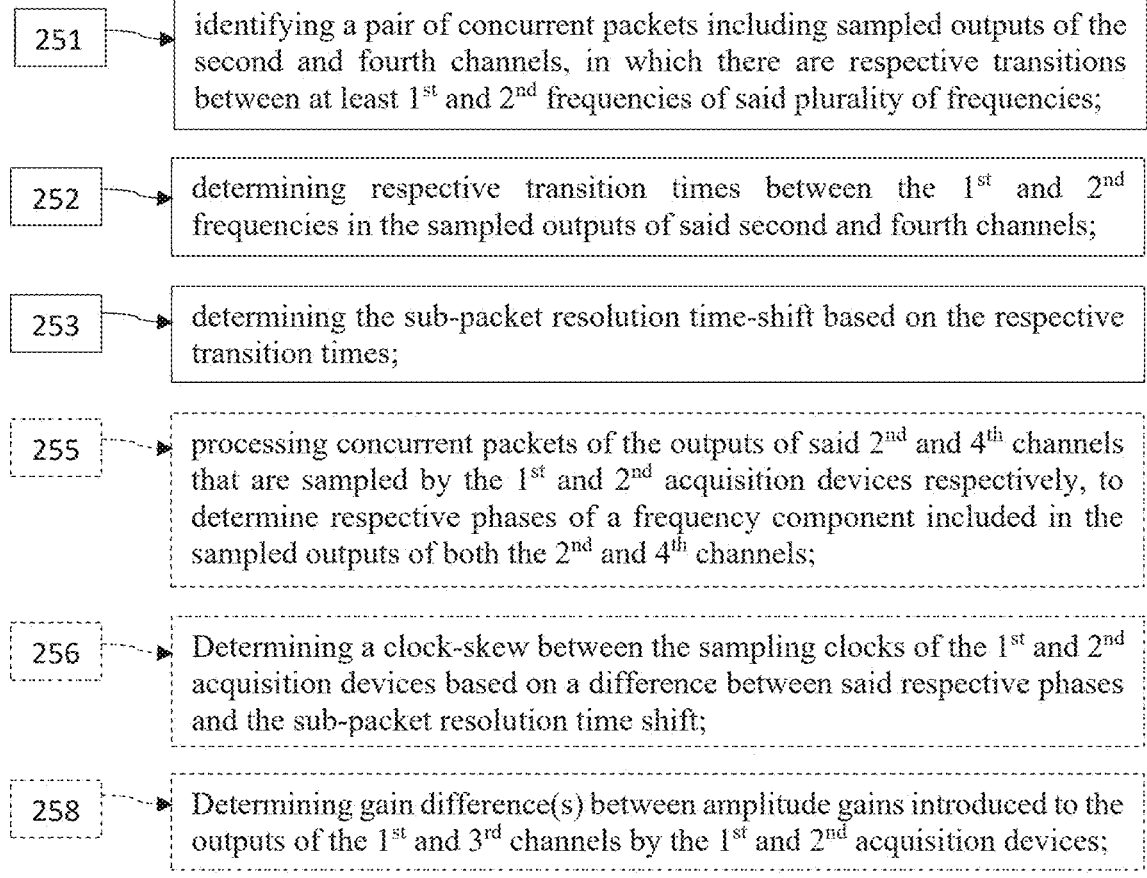

251 — identifying a pair of concurrent packets including sampled outputs of the second and fourth channels, in which there are respective transitions between at least $1^{st}$ and $2^{nd}$ frequencies of said plurality of frequencies;

252 — determining respective transition times between the $1^{st}$ and $2^{nd}$ frequencies in the sampled outputs of said second and fourth channels;

253 — determining the sub-packet resolution time-shift based on the respective transition times;

255 — processing concurrent packets of the outputs of said $2^{nd}$ and $4^{th}$ channels that are sampled by the $1^{st}$ and $2^{nd}$ acquisition devices respectively, to determine respective phases of a frequency component included in the sampled outputs of both the $2^{nd}$ and $4^{th}$ channels;

256 — Determining a clock-skew between the sampling clocks of the $1^{st}$ and $2^{nd}$ acquisition devices based on a difference between said respective phases and the sub-packet resolution time shift;

258 — Determining gain difference(s) between amplitude gains introduced to the outputs of the $1^{st}$ and $3^{rd}$ channels by the $1^{st}$ and $2^{nd}$ acquisition devices;

*FIG. 4B*

SYSTEMS AND METHODS OF POSITION SENSING

TECHNOLOGICAL FIELD

The present invention is in the field of medical devices and particularly relates to determining the positions of multiple medical devices and/or of instruments thereof during medical procedures.

BACKGROUND

A wide range of medical procedures involve a plurality of medical devices on and/or within a patient's body. The medical devices may be for example one or more catheters, and in many cases a single catheter includes a plurality of portions/sections, which may be for example one or more flexible sections (such as flexible arms/splines thereof) and/or medical instruments which may be distributed on the flexible sections (e.g., sensors/probs, electrodes such as EEG electrodes, ablation instruments and/or other instruments). During a medical operation tracking the positions of multiple medical devices/catheters and/or of multiple flexible sections of a medical device, which may be flexed/bent to approach/contact (sense/treat) different parts of a patient's anatomy, is often desired. One medical procedure in which the use of multiple catheters, and/or of catheters including a plurality of flexible sections/portions have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Often in such procedures, one or more catheters having a plurality of portions such as flexible sections/splines, are inserted into the patient body. In some cases, medical instruments arranged on the plurality of portions are operated for carrying out multiple interrelated operations such as electrocardiogram (ECG) mapping, tissue ablation, temperature sensing/mapping and/or image/ultrasound sensing. Some catheters are dedicated for placement in specific parts of the anatomy, e.g., heart chamber, coronary sinus, esophagus, atrium, ventricle, and include multiple flexible sections/portions that can conform to the shape of the anatomy of the treated body part, and optionally having a plurality instrument arranged at the different portions.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 4A is a flow diagram exemplifying a method 200 to determine positions of a plurality of position sensors of one or more medical devices, which are connected to different (e.g. $1^{st}$ and $2^{nd}$) signal acquisition devices, according to embodiments of the present invention;

FIG. 4B is a flow diagram of a synchronization method 250, which is used in some embodiments of the method 200 of FIG. 4A to determine synchronization parameters, and to thereby synchronize between the signal outputs of position sensors of the one or more medical devices, which are sampled/acquired by the different (e.g. $1^{st}$ & $2^{nd}$) signal acquisition devices.

Figure 1:
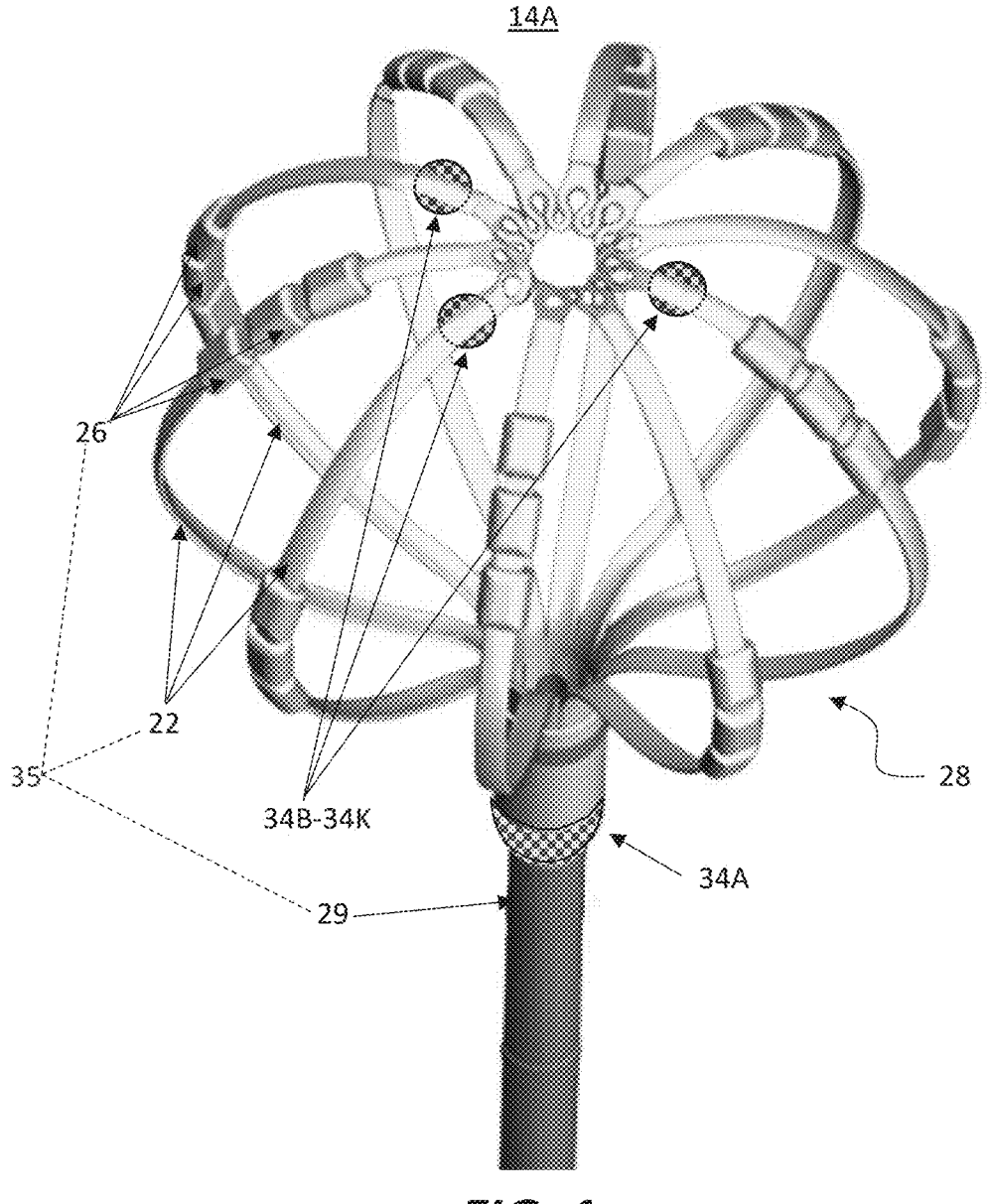
FIG. 1 is a schematic illustration of a catheter 14A having multiple portions/medical instruments at a distal end thereof and position sensors associated therewith.

Like reference numerals are used in the figures to designate similar modules/elements of the present invention or elements/modules having like functionalities. Accordingly, unless otherwise specified, description of modules/elements with reference to a certain embodiment of the invention should be understood to apply to all embodiments of the present invention in which such module/element is incorporated.

DETAILED DESCRIPTION OF EMBODIMENTS

With advancements of medical technologies, the number of medical devices and medical instruments thereon which are involved in a medical procedure and placed or moved, within the patient's body has increased significantly. For example, in some medical procedures, more than one catheter, such as intracardiac ECG mapping catheters and/or ablation catheters are used concurrently in a same procedure. Additionally, some catheters may have a plurality of movable/flexible sections (e.g., splines) with medical instruments thereon are used. The term medical instrument is used herein to encompass a medical device and/or a part/portion of a medical device that provides a certain medical function such as probing/sensing and/or treating a certain medical condition. For example, in many cases the medical instruments are arranged at various movable/flexible sections of the catheter's distal tip, such as the shaft, distal end effector, splines and/or at various other sections of the distal end effector thereof. The movable/flexible sections of the catheter may be adapted for flexing/expanding during the medical procedure (e.g., in order to accommodate the volume of the treated/monitored body anatomy and/or for bringing medical instruments thereon into contact or close proximity, with the wall/boundary of the treated/monitored body anatomy). Such techniques are used for example in order to enable mapping and/or treating several tissue regions of the anatomy substantially simultaneously. To this end, a large number of medical instruments, such as ECG electrodes, ablation utilities/instruments or other instruments, which may be arranged at a plurality of movable/flexible sections of a catheter, may for example be used by a physician to simultaneously capture/map the electrical activity from multiple locations in the heart chamber and/or or to simultaneously ablate specific tissue regions thereof.

A perspective view exemplifying such a medical device 14, in this non-limiting case an ablation catheter 14A, is shown in FIG. 1. The ablation catheter 14A includes a shaft/body 29 having a distal end 28 with a plurality of medical instruments 26 at a distal end part/region 28 thereof. The distal end 28 in this specific multi-instrument catheter example, includes multiple flexible sections 22 (hereinafter also referred to as splines) with multiple position sensors 34 arranged/coupled thereto at multiple locations (typically at least one sensor located on the shaft 29 and several sensors located on the splines 22 from the inner sides thereof). In the non-limiting example, the flexible sections 22 are connected to one another in a "basket" like form.

The distal end 28 includes multiple medical instruments 26 (e.g. ablation electrodes in this specific non-limiting example). The medical instruments 26 or some of them are arranged on the flexible sections 22, which form of an expandable assembly that can be deflectable outwardly from the catheter 14A (e.g. by moving a pusher rode) to move the medical instruments 26 to approach/contact the tissue wall of the heart for ablation of desired regions of the tissue. The positions of at least some of the medical instruments 26 can be tracked based on locations signals sensed by the position sensors 34. For clarity, in the following, the phrase distal end portions of a medical device/catheter, is used to designate portions/elements/sections of the medical device that are arranged at a distal end 28 of a medical device/catheter, and whose positions should be determined during a medical procedure. In this regard it should be understood that the phrase distal end portions may encompasses any one of: the shaft/body 29 of the medical device, the flexible/movable section(s) 22 thereof (if exist), the medical instruments 26 thereon, and/or the position sensors 34 capable of providing data/signals indicative of the positions of any of these elements. The term position is used herein to designate any one of a location, orientation or both, of a medical device and/or of a medical instrument or other distal end portion thereof. For instance, in some case there may not be a need to determine the location of a medical-device or of a medical instrument, but only its orientation, or vice-versa, and the system of the present invention may be adapted/operable to achieve the same.

The catheter 14A, illustrated in FIG. 1 presents a non-limiting example of a multi-instrument medical device. Other medical devices which can be used in the invention may include for instance other catheters which may have one or a plurality of medical instruments thereon (with or without flexible/movable sections), for instance an Intracardiac Electrogram (IEGM) sensing catheter such as 14B exemplified in FIG. 2 whose medical instruments 26 include near-field intracardial electrogram sensors/electrodes arranged on flexible/movable sections 22.

In order to perform medical procedures involving the plurality of medical devices/instruments with accuracy, the positions of the plurality of medical devices/instruments, should be monitored/tracked within the anatomy of the patient. In particular in many cases their positions relative to one another should be accurately determined. The position sensors 34 of the medical devices 14 are capable of receiving location signals (e.g., electromagnetic/magnetic signals) by which their respective positions and/or positions of multiple medical instruments 26 thereof can be determined. Accordingly, valuable information about the positions of different medical devices 14 and/or of the instruments 26 thereof, and in particular their relative positions between them, can be determined and provided/presented to the physician during the medical procedure (e.g., in real-time).

Therefore, there is a need in the art for systems and methods to enable determining the positions of large plurality of position sensors arranged at one or more distal end portions of one or more catheters or other medical devices. Conventional hardware for determining the positions of medical devices/instruments, are often limited in the capacity of the number of positions sensors whose positions can be determined thereby. To this end, the conventional hardware of medical device position sensing is generally not suited for connecting to medical devices/catheters, which have large pluralities of position sensors. Indeed, the conventional hardware typically includes transmitters for transmitting the location signals that can be received by the plurality position sensors of such catheters or other medical devices, but has limited channels for collecting the received locations signals sensed by the plurality of position sensors of such devices, and cannot accommodate simultaneous processing of location signals provided from large pluralities of positions sensors embedded in some types of advanced medical devices, such as spline or basket type catheters.

The present invention provides novel systems and methods for solving these problems. The technique of the invention facilitates extending the capabilities of existing medical device positioning hardware to enable determining the positions of multiple distal-end-portions/medical-instruments of medical devices (e.g., simultaneously), while optionally utilizing and in synchronization with, location signals that are collected through channels of conventional medical device positioning hardware that may already be in-use/deployed in the operation room (e.g. obviating a need to replace or obsolete the existing hardware). Advantageously the invention facilitates the positioning of relatively large pluralities of position sensors which may not be facilitated by the conventional already deployed positioning hardware, while without a need to replace existing location signal transmitters used, without transmission of additional location signals, and without replacing existing position signal acquisition devices. The technique of the present invention facilitates extending the number of the position signal acquisition channels of the already deployed positioning hardware, by adding additional signal acquisition device(s) capable of acquiring position signals from additional position sensors while operating in synchronization with existing/already-deployed, position signal acquisition devices. Accordingly, the positions of large number of medical instruments may be determined during a medical procedure in cost effective manner, without overcrowding the medical facilities with additional electromagnetic signals, and without costly replacements of the existing devices.

Figure 2:
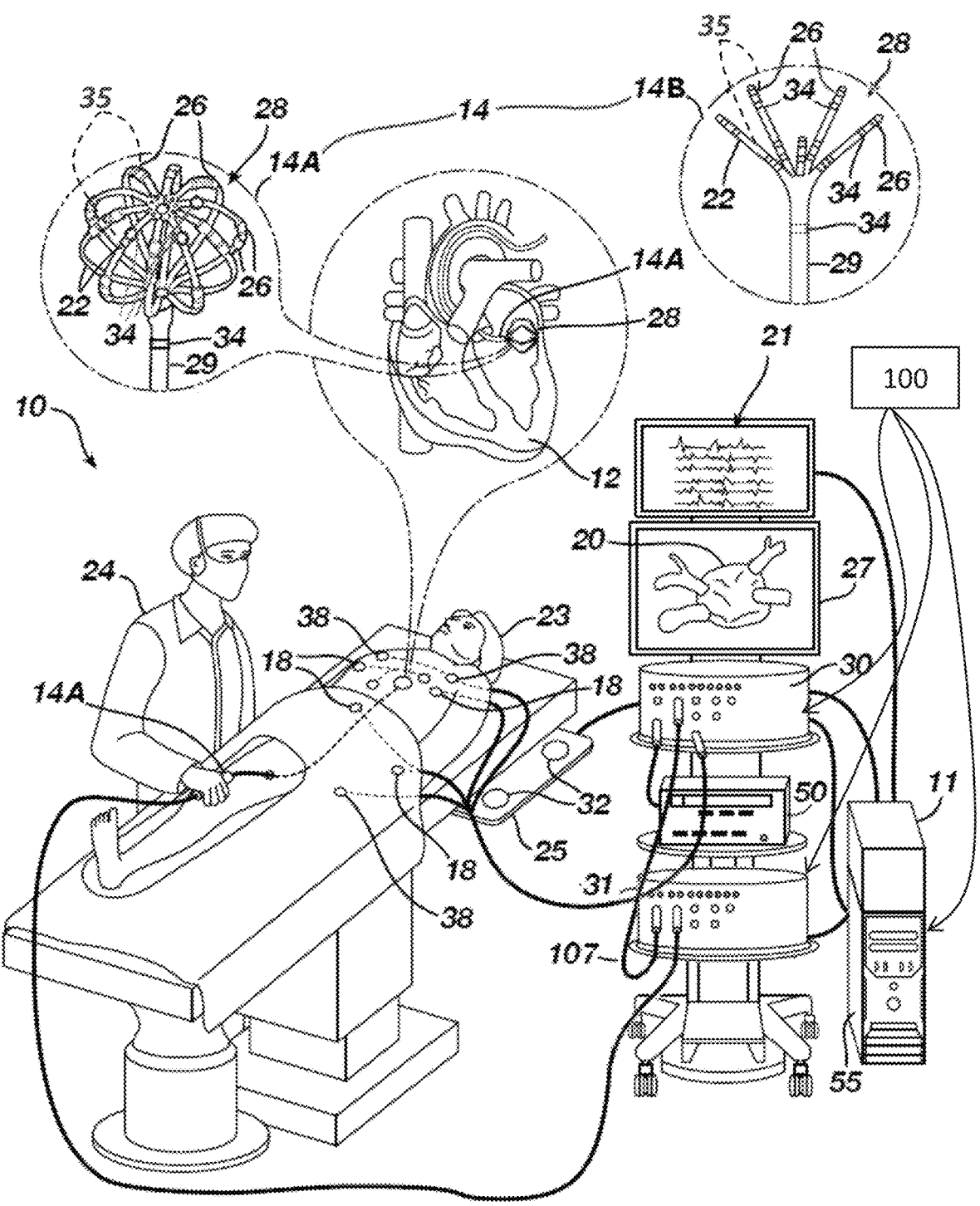
FIG. 2 is a schematic illustration showing a catheter-based mapping and ablation system 10 according to an embodiment of the present invention.

Reference is made to FIG. 2 showing an example catheter-based mapping and ablation system 10 deployed in a medical operation room. System 10 includes a positioning system 100 according to the present invention which includes, or is connectable to, multiple medical devices 14, such as catheters 14A and 14B, whose positions, and/or the positions of the various medical instruments 26 thereof, should be determined by the positioning system 100.

During operation, one or more of the medical-devices (e.g. catheters) 14 may be percutaneously inserted by a physician 24 through the patient's vascular system into a chamber or vascular structure of a heart 12. Typically, a delivery sheath catheter is inserted into the left or right atrium near a desired location in heart 12. Thereafter, one or more of the medical devices 14 may be inserted into the delivery sheath catheter so as to arrive at the desired location in heart 12. Physician 24 may place a distal end 28 of any of the medical-devices/catheters 14 such that medical instrument(s) 26 thereof, approach/contact the heart wall for probing/treating target site(s) in heart 12 (in cases where the medical instrument(s) 26 are arranged on flexible/movable sections 22 the later can move/flex to being the medical instrument(s) 26 to contact the tissue). For example, as indicated above, the system 10 may include a medical-device/catheter 14B dedicated for sensing Intracardiac Electrogram (IEGM) signals, and a medical-device/catheter 14A dedicated for ablating the tissue. It should be understood that the system 10 of the invention is not limited to the specific medical devices 14A and 14B exemplified illustrated in the figure and may be implemented with additional and/or other medical devices, for instance with a catheter that is dedicated for both sensing and ablating and/or with medical devices serving other purposes such as imaging.

System 10 may also include a recorder 11 adapted to record and display electrograms 21 captured with body surface electrocardiogram (ECG) electrodes 18 and intracardiac electrograms (IEGM) captured with ECG electrodes (e.g. instruments 26) of a medical device/catheter, such as 14B, that is adapted for sensing IEGM signals. Recorder 11 may include pacing capability for pacing the heart rhythm and/or may be electrically connected to a standalone pacer. System 10 may also include an ablation energy generator 50 that is adapted to conduct ablative energy to one or more of electrodes at a distal end of a medical-device/catheter, such as 14A, that is configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Often, for example in case of medical devices including complementary medical instruments 26, such as medical instruments for IEGM sensing and for tissue ablation (e.g. as in the example of 14B and 14A), it may be important to determine the relative positions between the medical instruments 26 (e.g. of the different functions) with accuracy, for instance in order to enable precise tissue ablation (e.g. by device 14A) at particular region(s) where abnormal IEGM was sensed (e.g. by device 14B).

Magnetic based position sensors 34 located on the medical-devices'/catheters' 14A and 14B distal ends 28, may be operated to provide data indicative of the real-time positions of the distal end portions 35 of the catheters during the medical procedure. The magnetic based position sensors 34 operate in conjunction with location pad 25 which includes a plurality of location signal transmitters 32 (e.g., magnetic coils) that generate/transmit electro-magnetic location signals (e.g., magnetic fields) in a predefined working volume surrounding the patient. The positions of the distal end 28 of the catheter 14A or 14B, and/or of the distal end portions 35 thereof, may then be tracked (e.g. in real-time) based on the electro-magnetic location signals that are generated with location pad 25 and sensed by magnetic based position sensor 34. The positions of other types of medical devices (e.g. a catheter with only single distal end portion or single medical instrument therein) and/or of other types of medical devices, may also be tracked by the system 10. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

System 10 typically includes a patient interface unit (PIU) 30, which is an interface configured to establish electrical communication between medical devices, such as catheters and/or other electrophysiological equipment, and a workstation 55 for controlling operation of system 10. The medical devices of system 10 include may include for example electrophysiological equipment such as one or more catheters 14, location pad 25, body surface ECG electrodes 18, electrode patches 38, ablation energy generator 50, and recorder 11. Workstation 55 includes memory, processor unit with memory or storage with appropriate operating software stored therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

As indicated above, typically, the PIU 30 typically implements processing capability for implementing real-time computations of positions of some of the medical devices/catheters 14 that are connected to the system 10. To achieve that the PIU 30 typically includes a location signal generator (e.g. transmitter—not specifically shown in FIG. 2; 132 in FIG. 3) that is connected to the location pad 25 and adapted to generate transmitted location signals TR (e.g. electromagnetic/magnetic location signals $TR_1$ to $TR_k$ with predetermined frequencies $F_1$ to $F_n$), which are provided to, and transmitted by, the location pad 25 in order for them to be sensed by the position sensors 34 of the medical devices 14. The PIU 30 also typically includes a signal acquisition device (e.g. receiver; not specifically shown in FIG. 2; 110 in FIG. 3) that is adapted to obtain location signals sensed by one or more of the position sensors 34 responsive to the location signal transmissions $TR_1$ to $TR_k$, apply real-time processing/preprocessing thereto, such as digitation/sampling and packaging thereof in communication packets (optionally also applying preprocessing operations such as filtration and/or amplification) and communicate the packets of the location signals to the workstation 55.

In turn, the workstation 55 is adapted to receive the sensed location signals in packets from the signal acquisition device of the PIU 30, and includes a positioning utility (e.g. not specifically shown in FIG. 2, 190 in FIG. 3; typically implemented in the workstation 55 by software), which is adapted to process the sensed location signals to determine data indicative of the positions of the position sensors 34, and thereby derive the positions of the medical devices 14 or of the medical instruments 26 thereon. As will be appreciated by those versed in the art, the positions of the position sensors 34 may be determined from the location signals sensed thereby, by determining the relative phases of the different frequencies $F_1$ to $F_n$ in the sensed position signals, relative to the phases of the respective frequencies in the location signal transmissions $TR_1$ to $TR_k$, and optionally may also be determined with improved accuracy based on the amplitudes of the different frequencies $F_1$ to $F_n$ in the sensed position signals.

However, in some implementations of systems 10 (e.g., systems already deployed in medical operation facilities), the PIU 30 may have limited number of input channels (CH1 in FIG. 3) for collecting and/or simultaneously sampling the sensed location signals and is not adapted to accommodate sufficient number of input channels for the multitude of position sensors which are included implemented in advanced medical devices 14 having a plurality of medical instruments 35 whose individual positions should be determined.

Therefore, according to the present invention, the system 10 includes an additional interface unit (AIU) 31 which includes an additional number of input channels (CH3 in FIG. 3) for collecting and/or simultaneously sampling the sensed location signals of additional medical devices/instruments. The additional interface unit 31 is configured and operable for complementing/extending the functionality of the PIU 30 with additional position sensing channels (CH3 in FIG. 3). The additional position sensing channels (CH3 in FIG. 3) of the AIU 31 enable to connect to the system 10 a plurality of position sensors, for which the channels of the PIU 30 may not be sufficient. Thus, in some implementations/medical-operations, as exemplified in FIG. 3, some of the position sensors 34 of one or more medical devices (e.g. 14B) may be connected to the input channels (CH1 in FIG. 3) of the PIU 30, and some of the position sensors 34 of one or more medical devices (e.g. 14A) may be connected to the input channels (CH3 in FIG. 3) of the AIU 31. Accordingly, the PIU 30 and AIU 31 are both implemented signal processing (e.g. sampling) for position signals from different position sensors.

In this regard, it is noted that in some embodiments, the PIU 30 may be part of an already deployed system 10, and the AIU 31 may be an addition to the deployed system 10, which may be added to facilitate the position sensing from additional plurality of position sensors 34 not accommodated by the PIU 30. Therefore, unless the PIU 30 and AIU 31 are synchronized with one another, their respective samplers may operate with clock delays (clock skew) between them, and/or may introduce somewhat different amplitude gains to the position signals sampled thereby. Such lack of synchronization may pose difficulty in determining the accurate positions of the position sensors 34 processed by the PIU 30 and/or the AIU 31. In particular, with the lack of synchronization, the relative positions between position sensors that are connected to the PIU 30 and AIU 31 (e.g. 34.1 and 34.2 in FIG. 3) may not be determined with sufficient accuracy. This may be problematic for example in case the medical instruments 26, whose position signals are processed by the PIU 30 and AIU 31, are complementary instruments (e.g. IEGM sensing and ablation instruments) whose relative positions are important for the accurate performance of the medical procedure.

Figure 3:
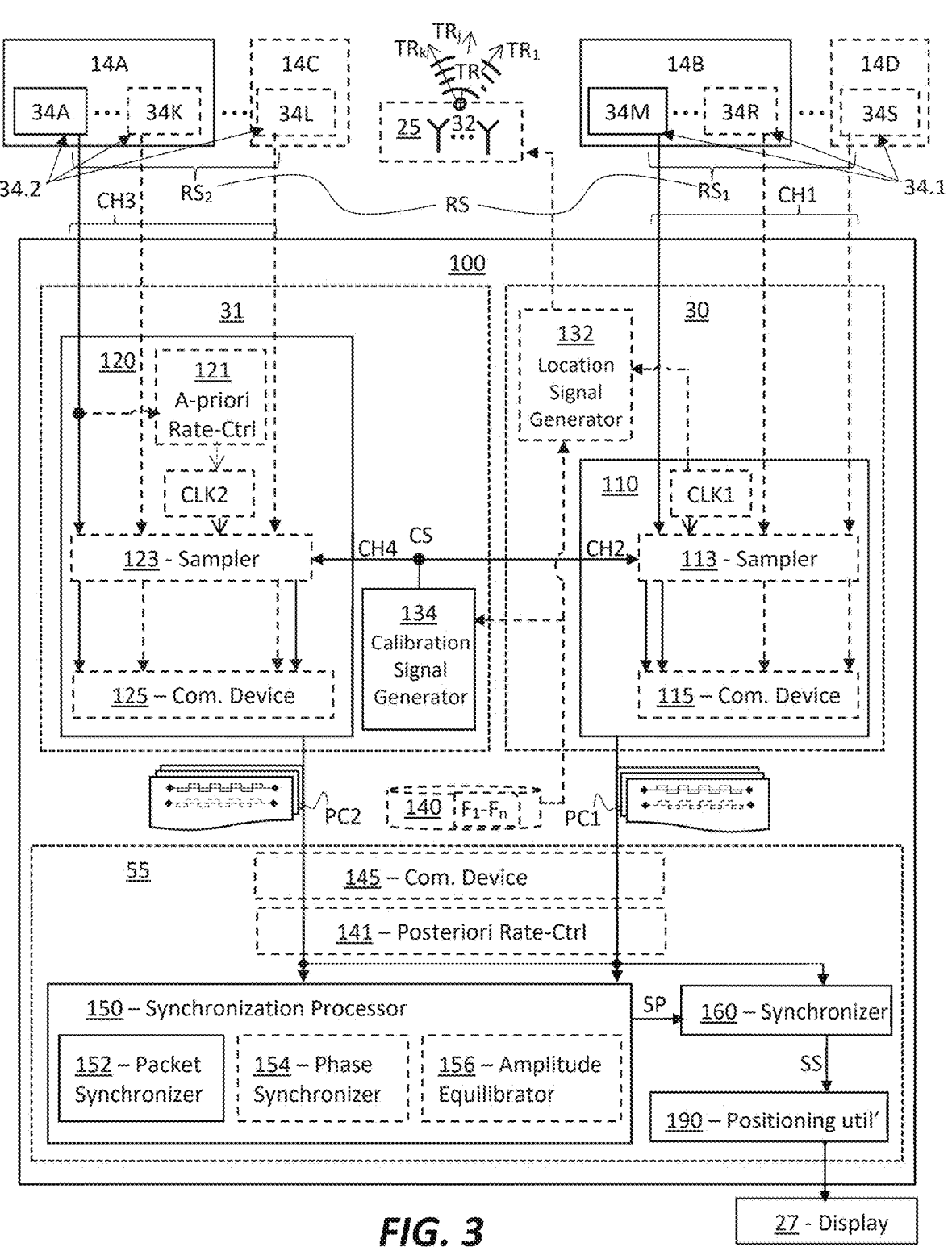
FIG. 3 is a block diagram illustrating the configuration of a positioning system 100 according to an embodiment of the present invention.

Therefore, according to the present invention the system 10 includes a synchronization processor and a synchronizer which are adapted to respectively determined synchronization parameters and synchronize between the position signals sampled by different sampling utilities PIU 30 and AIU 31 (in this example, see for instance FIG. 3, by the signal acquisition devices 110 and 120 of the PIU 30 and the AIU 31 respectively). In the non-limiting example of FIG. 2 the positioning system 100 includes: the PIU 30 and the AIU 31, which both implement/include respective signal acquisition devices (110 and 120 in FIG. 3), and the synchronization processor and the synchronizer (150 and 160 respectively in FIG. 3. The positioning system 100 may typically also include a positioning utility (not specifically shown in FIG. 2; 190 in FIG. 3), which is adapted to process the position signals and thereby determine the positions of the position sensors 34 or of medical instruments associated therewith. The synchronization processor 150 and the synchronizer 160, as well as the positioning utility 190), are not specifically shown in FIG. 2 but are implemented in the non-limiting example of FIG. 2 as part of the workstation 55.

In this regard, it should be noted that the workstation 55 may be implemented by a computerized system (e.g. by a general-purpose computer) with suitable software installed thereon. To this end, advantageously, deployment of the system 10 and/or 100 of the present invention, on an already deployed medical system, such as 10, which lacks sufficient number of channels for position sensors' signals, may be achieved by adding/connecting the additional interface unit

31 to the already deployed medical system 10, and optionally updating the software of the deployed medical system's workstation 55, to include/implement the synchronization processor 150 and/or include/implement the synchronizer 160 therein. In some embodiments the positioning utility 190, may not require any updates and may operate regularly to determine the positions of the position sensors based on the synchronized signals.

For instance, the additional interface unit 31 may facilitate connecting additional medical devices, such as catheters 14A and/or 14B, whose positions, or the positions of some distal end portions 35 thereof (e.g. of medical-instruments 26) should be tracked by the system 10. In turn, the synchronization processor (150 in FIG. 3), is adapted to utilize the calibration signal sampled by the respective signal acquisition devices (110 and 120 in FIG. 3) of the PIU 30 and AIU 31, to determine synchronization parameters (SP in FIG. 3) between the position signals that are respectively acquired/sampled thereby. The synchronizer (160 in FIG. 3), then utilizes the synchronization parameters SP to synchronize between the position signals acquired from the position sensors 34 by the respective signal acquisition devices (110 and 120 in FIG. 3), so the positions of medical instruments 26 associated respectively therewith, can be accurately presented (e.g. displayed to physician 24) with proper relative spatial and temporal relation to one another. The positioning utility (190 in FIG. 3) is adapted to utilize the process the synchronized signals obtained from the synchronizer, and based on the synchronized signals determine the respective positions of the position sensors 34 connected to PIU 30 and AIU 31, or the positions of distal end portions 35 of interest of the medical devices 14, to provide the same for presentation to the physician on the display 27.

Reference is now made together to FIGS. 3 and 4A which respectively illustrate the positioning system 100 and method 200 according to some embodiments of the present invention. FIG. 3 is a block diagram of a positioning system 100 according to an embodiment of the present invention, which may be implemented by the system 10 exemplified in FIG. 2; FIG. 4A illustrates a flow diagram of the method 200 according to embodiments of the present invention, which is implemented by the positioning system 100 in order to determine positions of a plurality of position sensors 34A-34S in one or more medical devices 14. More specifically, these system and method provide provides for accurately determining the relative positions between a plurality of position sensors which may connected to different (e.g. $1^{st}$ and $2^{nd}$) signal acquisition devices.

The system 100 includes a first and second signal acquisition devices 110 and 120, each configured and operable to receive and sample and pack the outputs from one or more position sensors 34, over one or more respective channels, and provide packets thereof for further processing by the system 100, which in turn determines thereby the positions of the respective sensors 34. In some embodiments, the first signal acquisition device 110 is incorporated as part of the PIU 30 of the system 10, which may have been already deployed in medical facilities, and the second signal acquisition device 120 is incorporated as part of an additional interface unit 31, which can be added to an already deployed system 10, in order to, at least inter-alia, extend the number of channels by which sensed position signals can be received and processed from the plurality of medical devices' position sensors 34. System 100 also includes a calibration signal generator 134 that is adapted to generate a calibration signal CS in the form of a continuous wave (CW) whose frequency is switched between a plurality of frequencies.

Optionally the calibration signal generator 134 may also be incorporated as part of the additional interface unit 31. As described in more details below, the calibration signal CS serves for synchronization between the outputs (sensed position signals) $RS_1$ and $RS_2$ of the respective one or more position sensors 34.1 and 34.2 which are received respectively by the first and second signal acquisition devices 110 and 120. To this end, system 100 also includes a synchronization processor 150, which is adapted to utilize the calibration signal CS to determined synchronization parameters SP for synchronizing between the sensed position signals $RS_1$ and $RS_2$ that are respectively sampled and packed by the two signal acquisition devices 110 and 120. System 100 further includes a synchronizer 160 that synchronizes between the position signals $RS_1$ and $RS_2$ acquired by the first and second signal acquisition devices 110 and 120 according to the synchronization parameters SP, and yields synchronized position signals SS. The system 100 also includes a positioning utility 190 that is adapted to process the synchronized position signals SS to determine the relative positions of the position sensors 34 (e.g. in sync with one another regardless of the specific acquisition device, 110 and/or 120, by which they were sampled and packed). The relative positions may be concurrent positions of the position sensors 34.1 and 34.2 and/or their positions at different times (for instance in case at a first time one medical device, e.g. 14B, acquires IEGM measurements from one or more locations, and at another time a second medical device e.g. 14A, should be operated to ablate certain of these locations). In some embodiments the positioning utility 190 is further adapted stream data indicative of the concurrent/relative positions of the position sensors 34, and/or of medical instruments 26 associated therewith, to the display 27 of system 10. In some embodiments, the synchronization processor 150 and/or the synchronizer 160, are incorporated as part of the workstation 55 of the system 10, which may have been already deployed in medical facilities. In some implementations also the positioning utility 190 is incorporated as part of the workstation 55.

In the specific none-limiting example of FIG. 3, the system 100 is illustrated connected to several medical devices including 14A and 14B, and optionally also to 14C and 14D. The medical devices 14A, 14C, 14B and 14D optionally include respectively the plurality of position sensors 34A to 34K, 34L, 34M to 34R and 34S. In this example, the outputs of the one or more position sensors 34M to 34R and 34S, which are collectively referenced herein as first position sensor(s) 34.1, are respectively connected to the first signal acquisition device 110 (e.g. of the PIU 30) via first input channels CH1 (e.g. these first channels are typically associated with respective input ports of the PIU 30). The first signal acquisition device 110 is also connected, via a second channel CH2 (e.g. a channel associated with another input port of the PIU 30) to the calibration signal generator 134 to receive the calibration signal CS. Optionally in some embodiments, as indicated above, the PIU 30 with the first signal acquisition device 110 is an already deployed module of the system 10, which was not a-priori designed to be connected to the calibration signal generator 134. Therefore, in such embodiments the second channel CH2, to which the calibration signal generator 134 is connected, is any one of the existing channels of the first signal acquisition device 110, which may have been originally designed to receive the output of a certain position sensor.

In this example, the outputs of the one or more position sensors 34A to 34K and 34L, which are collectively referenced herein as second position sensor(s) 34.2, are respectively connected to the second signal acquisition device 120 (e.g. of the additional interface unit 31) via third input channels CH3 (e.g. these third channels are typically associated with respective input ports of the additional interface unit 31). The second signal acquisition devices 110 is also connected, via a fourth channel CH4 to the calibration signal generator 134 to receive the calibration signal CS. Optionally, as indicated above the additional interface unit 31 includes both of the second signal acquisition device 120 and the calibration signal generator 134, and thus the fourth channel CH4 connecting between the them may be an internal channel of the additional interface unit 31, e.g. not associated with an external input port of the additional interface unit 31.

It would be appreciated that the number of medical devices 14 and the number of position sensors included in each, which are connected to the system are provided herein only by way of a non-limiting example. For instance, the system 100 may be connected to a plurality of medical devices each having only one position sensor thereon or each having a plurality of position sensors thereon.

The operation of the system 100 will now be described in more details with reference to the method 200 to determine the positions of the medical devices or of portions thereof (e.g. the medical instruments thereon, or otherwise of the portions thereof at which the position sensors 14 are connected), according to an embodiment of the present invention illustrated in FIG. 4A. The method 200 particularly facilitates for synchronizing between the position signals of the first and second position sensors 34.1 and 34.2, so that their respective concurrent/relative positions, or the respective concurrent/relative positions of medical instruments 26 associated therewith, or inferred therefrom, can be determined and presented with accuracy to the physician 24 (e.g. on display 27).

Optionally prior to the method 200, the signal sampling rate of at least one of the first and second signal acquisition devices 110 and 120 is adjusted (equated) such that the signal sampling rates of the first and second signal acquisition devices 110 and 120 are substantially equal. In some embodiments, this operation is performed for example by an optional a-priori rate-controller 121 that may be included in one of the signal acquisition devices, e.g. included the second signal acquisition device 120 which may be added to an already deployed system 10. In this regard, it is noted that typically the first and second signal acquisition devices 110 and 120 are respectively associated with respective first and second signal clocks CLK1 and CLK2, by which their respective sampling rates are dictated. The PIU 30 (e.g. of an already deployed system 10) typically includes the first signal acquisition device 110 and the location signal generator 132, as well as the first signal clock CLK1 which is used thereby for both adjusting/dictating the sampling rate of the first signal acquisition device 110 as well as for controlling the generation of the transmitted location signals TR by the location signal generator 132 such that they are generated with the predetermined frequencies $F_1$ to $F_n$ relative-to/based-on the rate of the first signal clock CLK1. Accordingly, in some embodiments the a-priori rate-controller 121 determines the rate R1 of the first signal clock CLK1 utilizing the one or more of the sensed location signals $RS_2$ which are received thereby over the channel CH3. The a-priori rate-controller 121 of the second signal acquisition device 120 processes those one or more received signals, based on the second signal clock CLK2, to determine one or more of the received frequencies $F^r_1$ to $F^r_n$ contained therein based on the rate R2 of second signal clock CLK2. The processing may for example include spectral analysis of those one or more received signals (e.g. by Fast Fourier Transform, FFT, and/or any other spectral analysis process which might be considered more suitable/efficient for this purpose by a person skilled in the art). The a-priori rate-controller 121 determines the ratio R≡R1/R2 between the rates R1 and R2 of the first and second clock, based on the ratio between at least one received frequency $F^r_i$ of the received frequencies $F^r_1$ to $F^r_n$ as determined relative to the rate R2 of second signal clock CLK2 and a corresponding predetermined frequency $F_i$ of the predetermined frequencies $F_1$ to $F_n$ with which the transmitted signals TR utilizing the rate R1 of the first clock CLK1. For instance, the ratio R between the first and second clock rates R1 and R2 can be determined as R≡R1/R2=$F^r_i$/$F_i$. In this regard it is noted that in case the difference in the clock rates R1 and R2 is smaller than the differences between the predetermined frequencies $F_1$ to $F_n$, the correspondence between the received frequencies $F^r_1$ to $F^r_n$ and the predetermined frequencies $F_1$ to $F_n$ of the transmissions TR, may be identified by considering the closest frequencies in the received and predetermined frequencies to be matching/corresponding-to-one-another. Otherwise, in case the difference in the clock rates R1 and R2 is larger than the differences between the predetermined frequencies $F_1$ to $F_n$, such correspondence may be determined by systematically matching each of the predetermined frequencies $F_1$ to $F_n$ to one the received frequencies $F^r_1$ to $F^r_n$ such that the same ratio R=$F^r_i$/$F_i$ is maintained consistent for all the corresponding pairs of received and predetermined frequencies. Thus, once the R≡R1/R2 is determined, the sampling rate of the sampler 123 of the second signal acquisition device 120 may be adjusted according to that ratio R (e.g. by increasing/decreasing the sampling rate, or the rate of the second signal clock CLK2, by a factor of that ratio R), and thereby equating the sampling rates of R1 and R2 of the first and second signal acquisition devices 110 and 120.

It should be noted that optionally instead of an a-priori adjustment of the sampling rates R1 and R2 of the first and second signal acquisition devices 110 and 120, a posteriori sampling rate adjustment/compensation may be applied to signal samples of at least one of the first and second signal acquisition devices 110 and 120 in order to compensate for the different sampling rates thereof (e.g. the may be performed for instance by re-interpolation of signal samples of at least one of the signal acquisition devices). In this case, the samples of the signals in the packets PC1 and/or PC2 that are sampled by at least one of the first and second signal acquisition devices 110 and 120 are adjusted in order to compensate for the difference in their respective sampling rates R1 and R2. For instance, in some implementations the ratio R=R1/R2 between the sampling rates R1 and R2 may be determined by the posteriori rate controller 141 in somewhat similar manner as described above with reference to-priori rate-controller 121 (e.g. applying spectral analysis to one or more portions of the signals received from the first and second acquisition devices 110 and 120 to identify ratio between like frequencies sampled respectively thereby and determining the ratio R=R1/R2 accordingly). Then the posteriori rate controller 141 may adjust the samples of the signals of at least one of the packets PC1 and/or PC2 in order to compensate for the difference/ratio R in the sampling rates. For example, compensating for the difference in the sampling rate may be achieved by re-interpolation of the signals samples in at least one of the packets PC1 and/or PC2 e.g. to spread/squash the samples thereof, according to the ratio R.

It should be noted that equating/compensating—for the different the sampling rates R1 and R2, as described above by either a-priori or posteriori processes, may be performed only once, and/or it may be performed from time to time in order to re-equalize the sampling rates of R1 and R2 in case the they are drifted over time.

In operation 210 of the method 200, the calibration signal CS (also referred to herein as dummy signal) is generated by the calibration signal generator 134 in the form of a continuous wave (CW) with frequency that is switched between a plurality of frequencies. For example, typically the plurality of frequencies between them the frequency of the calibration signal CS is switched, include one or more, or all, of the predetermined frequencies $F_1$-$F_n$ that are generated in the transmitted location signals TR by the location signal generator 132. The calibration signal generator 134 may be a-priori configured to generate the calibration signal CS with those frequencies, and/or may be adapted to utilize reference data indicative thereof, which may be stored in a data repository 140 accessible by the calibration signal generator 134.

In operations 220 and 230, location signal outputs $RS_1$ and $RS_2$ from the respective first and second position sensors 34.1 and 34.2, and the calibration signal CS are received, sampled and packed by the first and second signal acquisition devices 110 and 120. More specifically, in 220 the first signal acquisition device 110 (e.g. a sampler 113, such as an A/D converter, thereof) concurrently samples the location signal output(s) $RS_1$ of at least one first position sensor 34.1, which is received thereby over at least one first channel CH1, and the calibration signal CS, which is received over the second channel CH2. The first signal acquisition device 110 (e.g. a network communication device 115 thereof) than packs data indicative of the sampled signals from the at least one first channel CH1 and the second channel CH2 in packets PC1. The data being packed in the packets PC1 may for example include the actual samples of the signals. Alternatively or additionally the first signal acquisition device 110 may be adapted to apply spectral processing to the sampled signals and designate properties of the frequency components included in the sampled signals, such as their respective frequencies, amplitudes, and phases, in the packets PC1. In like manner, in 230 the second signal acquisition device 120 (e.g. a sampler 123, such as an A/D converter, thereof) concurrently samples the location signal output(s) $RS_2$ from at least one second position sensor 34.2, which is received thereby over at least one third channel CH3 and the calibration signal CS received over the fourth channel CH4. The second signal acquisition device 120 (e.g. network communication device 125 thereof) than packs data indicative of the sampled signals from the at least one third channel CH3 and the fourth channel CH4 in packets PC2. Also here, the data being packed in the packets PC2 may for example include the actual samples of the signals, and/or the second signal acquisition device 120 may be adapted to apply spectral processing to the sampled signals and designate properties of the frequency components thereor (e.g. the respective frequencies, amplitudes, and phases of the frequency components) in the packets PC2. The packets PC1 and PC2 are then communicated from the respective first and second signal acquisition devices 110 and 120 (e.g. by their respective network communication devices 115 and 125) to the synchronization processor 150. The packet communication may be performed over a network such as TCP based network (e.g. such as LAN, WAN, WiFi or other network), and may optionally be directed to the workstation 55, at which the synchronization processor 150 may optionally be implemented (e.g. via communication device 145 associated therewith).

In operation 250, the synchronization processor 150 determines synchronization parameters SP required for synchronizing between the position sensors' signals $RS_1$ and $RS_2$ that are sampled by the different signal acquisition devices. More specifically in this example, determining synchronization parameters for synchronizing between the signals sampled from each of the at least one first channel CH1 of the first acquisition device 110 and the at least one third channel CH3 of the second acquisition device 120.

FIG. 4B is a flow diagram of a novel synchronization method 250, which may be implemented in the method 200 of FIG. 4A (e.g. by the synchronization processor 150) in order to determine the synchronization parameters based on the calibration signal CS that is sampled by the first and second acquisition devices 110 and 120 respectively (i.e. by each of the at least second and fourth channels, CH2 and CH4, thereof).

In this regard, it should be noted that the sampling and packing, 220 and 230, of the position signals $RS_1$ and $RS_2$ by the first and second acquisition devices 110 and 120 are not necessarily concurrent, and/or may not be sufficiently timely aligned, for example due to a clock skew (e.g. clock delay), which might occur for example due to lack of synchronization between the signal clocks CLK1 and CLK2 of the first and second acquisition devices 110 and 120. For instance, even in case the clock rates of their sampling clocks CLK1 and CLK2 are adjusted to match, the ticks of one of the sampling clocks may be still be ahead or behind the ticks of the other clock, with timing misalignment ΔT between them. To this end, in some embodiments one of the synchronization parameters determined and compensated for by the synchronization processor 150 is the timing misalignment ΔT between the sampling and packing of signals processed by the first and second acquisition devices 110 and 120. In embodiments the synchronization processor 150 operates to determine the timing misalignment ΔT with sub-packet resolution by carrying out the operations 251, 252 and 253 of method 250 illustrated in FIG. 4B. In this regard it should be noted that the term sub-packet resolution is used herein to designate a temporal resolution with precision finer than the temporal durations/extents of the packets PC1 and PC2. Optionally, in some embodiments, the synchronization processor 150 further carries out the optional operations 255 and 256 to determine the timing misalignment ΔT with further improved resolution, e.g. with resolution in the order of the sampling rates of the signals. The timing misalignment ΔT may be determined by the synchronization processor 150 by processing the calibration signal CS, which is commonly received and sampled by the first and second acquisition devices 110 and 120 from over their respective second and fourth channels CH2 and CH4. The thus determined timing misalignment ΔT forms at least a part of the synchronization parameters SP, which are used in operation 260, by the synchronization processor 150, to synchronize between the position signals $RS_1$ and $RS_2$ that are sampled from each of the first and third channels CH1 and CH3 of the respective first and second acquisition devices 110 and 120.

In addition to timing misalignment, it should be noted that the acquisition devices 110 and 120 (e.g. their respective samplers 113 and 123, and/or optionally amplifiers thereof) may also introduce somewhat different amplitude gains to the sampled position signals $RS_1$ and $RS_2$ that are respectively sampled by the first and second acquisition devices 110 and 120 (e.g. due to hardware variability between the samplers 113 and 123, and/or amplifiers and/or due to variations in the input voltage/power they receive for their operation). To this end, in embodiments where the amplitudes of various frequency components in the position signals $RS_1$ and $RS_2$ are used by the positioning utility 190 to determine the positions of the position sensors 34.1 and 34.2, the synchronization processor 150 may carry also carry out the optional operation 258 of method 250 in order to determine difference(s) ΔG in the amplitude gains introduced by the first and second acquisition devices 110 and 120. In such embodiments the difference(s) in the amplitude gains ΔG also form a part of the synchronization parameters SP which are then used in operation 260 to synchronize between the position signals $RS_1$ and $RS_2$. Therefore in some embodiments, by processing the calibration signal CS, which is commonly sampled from over the second and fourth channels, CH2 and CH4 by the respective samplers 113 and 123 of the first and second acquisition devices 110 and 120, the difference ΔG in the amplitude gains introduced by the respective samplers 113 and 123 may be determined, and may be further used to adjust the position signals $RS_1$ and $RS_2$ that are also sampled by the same respective samplers 113 and 123 in order to compensate for this gain difference ΔG.

The synchronization operation 250 of FIG. 4A will now be described in more detail with reference to FIG. 4B. Operation/method 250 may optionally include several processes to determine one or more synchronization parameters for synchronizing between the position signals $RS_1$ and $RS_2$. A first process, which is also referred to herein as packet synchronization, may include for example the operations 251 to 253 (e.g. which may be performed by a packet synchronizer module 152 of the synchronization processor 150). The synchronization processor 150, e.g. the packet synchronizer module 152, may be adapted to carry out the operations 251 to 253 as follows:

251—identify, in the packets PC1 and PC2, a pair of substantially concurrent packets with samples from the second and fourth channels CH2 and CH4 (by which the calibration signal CS is received and sampled by the first and second acquisition devices 110 and 120), such that in both of the packets of the pair there exists a transition between at least at least a first frequency and a second frequency of the switched frequencies of the calibration signal CS. Here, the pair of substantially concurrent packets refers to a pair of packets both including/indicative-of samples of a common portion of the calibration signal CS. The pair of concurrent packets may be identified for example based on the count, order, and/or ordinal-numbers/indices, of the packets PC1 and PC2 received from the first and second acquisition devices 110 and 120 (e.g. without necessarily specifically looking into the contents of the packets).

252—As indicated above the calibration signal CS is a CW signal whose frequency is switched, e.g. periodically, between a plurality of frequencies. In operation 252, the pair of concurrent packets are processed to determine transition time between the at least first and second frequencies in the calibration signal CS in each of the concurrent packets. In other words, the frequency switching, serves as a temporal reference, based on which a temporal misalignment (clock skew) between the timings of the packaging of packets PC1 and PC2 by the first and second acquisition devices 110 and 120 can be inferred. Generally, the transition time between the at least first and second frequencies in each packet can be determined by various signal processing techniques (e.g. of instance by processing the samples of the signal in the packet in order to identify the sample index up to which the frequency of the sampled CW signal is the $1^{st}$ frequency and from which onward the $2^{nd}$ frequency). However, in some embodiments, this process may be performed efficiently by determining the respective powers of the $1^{st}$ frequency and $2^{nd}$ frequencies of the calibration signal portions sampled in each of the concurrent packets and taking their ratio. For instance, considering a packet indicative of a portion of total duration T of the calibration signal CS in which only two frequencies F1 and F2 of the CS calibration signal are included, the transition time t between those two frequencies relative to the beginning of the packet duration, may be inferred based on the relative powers P(F1) and P(F2) of the first and second frequency components in the packet as follows:

$$\frac{t}{T} = A\frac{P(F1)}{P(F1) + P(F2)}$$

where A is just a proportionality constant indicative of the relative powers of the F1 and F2 frequencies in the calibration signal CS (e.g. A is 1 for equal amplitudes). Accordingly, based on the packets' period T and the relative amplitudes A of the frequencies F1 and F2 in the calibration signal CS (which may generally be known/predetermined), the transition time t can be determined/estimated, at least up to a wavelength period of the signal, based on the powers of P(F1) and P(F2) of the F1 and F2 frequency components. As will be appreciated by those versed in the art, the powers of P(F1) and P(F2) of the F1 and F2 frequency components can be generally determined by computing a power spectrum of the packet. However, in some embodiments of the present invention the powers of P(F1) and P(F2) of the F1 and F2 frequency components are determined more efficiently by utilizing the known in the art Goertzel process, by which the powers P(F1) and P(F2) of specific frequencies F1 and F2 may be determined efficiently, based on predetermined information indicative of the specific frequencies F1 and F2 included in the calibration signal CS. Accordingly, in this manner in 252 the respective transition times $t_1$ and $t_2$ between the F1 and F2 frequency components of the calibration signal CS in each of the respective concurrent packets, are determined with sub-packet resolution, i.e. with resolution of at least one characteristic period of the frequencies F1 and F2 which is generally of shorted duration than the packets' durations (hence with sub-packet resolution).

253—Thus, once the respective transition times $t_1$ and $t_2$ between the at least two frequency components F1 and F2 of the calibration signal CS are determined for the concurrent packets with the sub-packet resolution, the sub-packet resolution time-shift/temporal-misalignment $\Delta t_P$ between the concurrent packets may be determined based on the respective transition times $t_1$ and $t_2$, typically by tacking the difference between them, e.g. $\Delta t_P = t_2 - t_1$.

In some embodiments, the sub-packet resolution time-shift $\Delta t_P$ may be sufficiently accurate; e.g., it may be determined in some implementations with sufficiently high resolution in the order of the time resolution of the sampling. Accordingly, in such embodiments the total temporal mis-alignment (clock skew) $\Delta t$ between the sampling and packing of the respective location signals $RS_1$ and $RS_2$ by the first and second acquisition devices 110 and 120 may be estimated to be substantially equal to the sub-packet resolution time-shift $\Delta t_P$: $\Delta t \approx \Delta t_P$.

However, in some other embodiments, resolution by which the sub-packet resolution time-shift $\Delta t_P$ is not sufficiently high to facilitate accurate determination of the concurrent positions of the position sensors 34.1 and 34.2. For instance, as indicated above, in some embodiments, efficient implementation the time shift between the packets PC1 and PC2 may be determined with sub-packet resolution, based on a ratio between powers of a frequency component of the calibration signal as sampled by the first and second acquisition devices 110 and 120. However, although resolving the time shift $\Delta t_P$ by this exemplified technique is efficient, in some implementations the resolution of the time shift $\Delta t_P$ provides, which is the order of less than the characteristic periodicities of the frequencies in the position signal, may not be sufficiently high (e.g. substantially lower than the sampling rate). In other words, in some embodiments the sub-packet resolution synchronization may be with precision finer than the characteristic time period of the frequency constituents in the location signals RS (e.g. sufficient to compensate for temporal mis-alignments in the between the "unwrapped" phases of the location signals $RS_1$ and $RS_2$ of the first and second position sensors 34.1 and 34.2, in the order of the time periods of the frequency constituents of the location signals RS).

To this end, in embodiments where the sub-packet resolution time-shift $\Delta t_P$ determined is only accurate to about the order of a characteristic period of the frequencies in the position signals RS, there may remain some residual temporal misalignment $\Delta t_S$ between the respective first and second location signals $RS_1$ and $RS_2$ whose duration is shorter than the characteristic periods of the frequencies in the position signals RS. In other words, in such embodiments it might not be sufficient to assert the total temporal misalignment $\Delta t$ (clock skew) between the sampling and packing of the respective location signals $RS_1$ and $RS_2$ to be about equal to the sub-packet resolution time-shift $\Delta t_P$ which is determined in 250A, and the residual temporal misalignment $\Delta t_S$ should also be inferred in order to determine/estimate the total temporal misalignment (clock skew) $\Delta t$ as: $\Delta t \approx \Delta t_P + \Delta t_S$.

Since this residual temporal misalignment $\Delta t_S$ is shorter than the characteristic period of the frequencies in the position signals RS, it can be inferred from the difference between the wrapped phases of a certain signal components that is sampled concurrently by both the first and second acquisition devices 110 and 120 (the term wrapped phase used herein refers to a phase of between $-\pi$ and $\pi$, i.e., smaller than one wavelength period). Therefore, in some implementations, optionally a further temporal synchronization process including operations 255 and 256 may be performed in order to determine the total temporal misalignment $\Delta t$ between the location signals $RS_1$ and $RS_2$ (e.g. with resolution in the order of the sampling/clock rate). This further temporal synchronization process which may be implemented for example by a phase synchronizer 154 module of the synchronization processor 150, may include for example the following:

255—processing a pair of substantially concurrent packets of the packets PC1 and PC2, which include samples of the calibration signal CS that are sampled by the first and second acquisition devices 110 and 120 from the second and fourth channels CH2 and CH4 respectively, to determine the residual temporal misalignment $\Delta t_S$. The pair of substantially concurrent packets may be for example the same pair of concurrent packets identified in operation 250A(a), or another pair of such concurrent packets (e.g. from different timing). The concurrent packets are processed, for instance by spectral analysis/processing, to determine a phase difference $\Delta\varphi_{Fi}$ between the phases of at least one a frequency component Fi commonly included therein. Although the spectral analysis/processing may generally be performed by any suitable known in the art technique to determine the phases $\varphi_1$ and $\varphi_2$ of the frequency component Fi in the respective concurrent packets of the packets PC1 and PC2 (e.g. by any suitable Fourier transform processing algorithm), preferably in some embodiments it is performed utilizing the Goertzel process. In this regard, it should be appreciated that the frequencies included in the calibration signal CS are generally known/predetermined, so utilizing the Goertzel process may leverage the predetermined frequency information to determine the phases of the common frequency component $F_i$ the concurrent packets, efficiently. Accordingly, the phase difference $\Delta\varphi_{Fi}$ can be determined based on the difference between the phases $\varphi_1$ and $\varphi_2$ of the frequency component Fi in the respective concurrent packets, for example by: $\Delta\varphi_{Fi}=\varphi_1-\varphi_2$.

Then, in 256, the clock-skew (total temporal misalignment) $\Delta t$ between the $1^{st}$ and $2^{nd}$ acquisition devices based on the phase difference $\Delta\varphi_{Fi}$ determined for the frequency Fi in operation 255 and the sub-packet resolution time-shift $\Delta t_P$ that is determined by operations 251 to 253. In this regard, in some embodiments in 255, at first the signals/samples in the pair of concurrent packets are timely shifted relative to one another to compensate for the sub-packet resolution time-shift $\Delta t_P$ between them, and then the spectral analysis/processing (e.g. such as Goertzel process) is carried out to determine their phases $\varphi_1$ and $\varphi_2$. In such embodiments the residual temporal misalignment $\Delta t_S$ may be determined in 256 for instance as follows:

$$\Delta t_S = \frac{\Delta\varphi_{Fi}}{2\pi * F_i}$$

Alternatively, in embodiments where the signals/samples in the pair of concurrent packets are not shifted relative to one another to compensate for the sub-packet resolution time-shift $\Delta t_P$ before determining their phases $\varphi_1$ and $\varphi_2$ are in operation 255, the residual temporal misalignment $\Delta t_S$ may be determined in 256 for instance as follows:

$$\Delta t_S = \frac{\Delta\varphi_{Fi}}{2\pi * F_i} - \left(\Delta t_P - \frac{\lfloor F_i * \Delta t_P\rfloor}{F_i}\right)$$

where the second term $$\left(\Delta t_P - \frac{\lfloor F_i * \Delta t_P\rfloor}{F_i}\right)$$

represents the part of the wrapped phase difference that is already included in the sub-packet resolution time-shift $\Delta t_P$.

Accordingly, in the optional process of operations 255-256 the total temporal-misalignment/clock-skew $\Delta t$ between the first and second acquisition devices 110 and 120 may be determined with improved accuracy (e.g. by considering both the sub-packet resolution time-shift $\Delta t_P$ determined by operations 251 to 253 and the residual temporal misalignment $\Delta t_S$ determined by operations 255 and 256, for example as follows: $\Delta t=\Delta t_P+\Delta t_S$.

To this end, the optional, operations 255 and 256 may be performed in order to determine the total temporal-misalignment/clock-skew $\Delta t$ between the first and second acquisition devices 110 and 120 (e.g. between their respective signal clocks) with resolution that is in the order of the sampling resolution. In some embodiments this may be based on the comparison between the phases of the calibration signal CS in the second and fourth channels CH2 and CH4, and can therefore compensate for mismatches between the wrapped phases of the signals. Since in typical embodiments in the time extent of the respective packets PC1 and PC2 are longer than a period of a characteristic wavelength in the signals, therefore in such embodiments the further temporal synchronization operations 255-256 may be performed only after the sub-packet resolution temporal synchronization operations 251-253 are performed, so that any unwrapped phase differences, which are longer than the characteristic wavelength's period, are removed/considered by these operations.

As indicated above, in some implementations the first and second acquisition devices 110 and 120 may also introduce somewhat different amplitude gains to the signals respectively processed thereby. Therefore, in embodiments where positioning utility 190 relies also on the amplitudes of the sensed position signals RS to determine the respective positions of the position sensors 34, the method 200 may further include an optional operation 258 for determining the difference(s) $\Delta G$ between the amplitude gains introduced to the position signals $RS_1$ and $RS_2$ by the first and second acquisition devices 110 and 120 respectively.

The operation 258 may be carried out for example by the amplitude equilibrator 156 module of the synchronization processor 150. To this end, operation 258 may include identifying at least one pair of packets of the packets PC1 and PC2 received from the first and second acquisition devices 110 and 120, which respectively include samples of the calibration signal CS that is respectively obtained by the first and second acquisition devices 110 and 120 via the outputs of the second and fourth channels CH2 and CH4. Then processing the pair of packets from the first and second acquisition devices 110 and 120 to identify the respective amplitudes A1 and A2 of at least one frequency component $F_i$ of the calibration signal which is commonly included in the pair of packets respectively. The processing to determine the respective amplitudes, may be carried out utilizing any suitable spectral analysis processing (e.g. Fourier Transform), and more preferably in embodiments where the frequency components in the calibration signal are a-priori known/redetermined, the Goertzel processing may be used in order to efficiently determine the amplitudes A1 and A2. Then the difference $\Delta G$ between the amplitude gains introduced to the sensed locations signals RS1 and RS2 by the first and second acquisition devices 110 and 120, may be determined for example based on the ratio between the amplitudes of the calibration signal sampled by the first and second acquisition devices 110 and 120, as follows: $\Delta G=A1/A2$.

In this regard, it should be noted that in some embodiments the gain difference between the gains introduced to the signals by the respective first and second acquisition devices 110 and 120, is frequency dependent. In other words, different frequency component of the predetermined frequencies $F_1$ to $F_n$ of the location signals RS may be amplified/suppressed differently by the first and second acquisition devices 110 and 120. In such embodiments the operation 258 may be adapted to determine a plurality of gain differences ΔG, including a respective gain difference $\Delta G_i$ per each frequency component $F_i$ of the predetermined frequencies $F_1$ to $F_n$ of the location signals RS.

To this end, in such embodiments, in the method operation 210 described above the calibration signal CS is generated by the calibration signal generator 134 as a CW signal whose frequency is switched between the plurality predetermined frequencies $F_1$ to $F_n$ of the location signals RS. Accordingly, in operation 258 for determining the gain difference(s), respective gain difference $\Delta G_i$ may be determined per each of the predetermined frequencies $F_1$ to $F_n$ that are generated in the transmitted location signals TR by the location signal generator 132. Determining the respective gain difference $\Delta G_i$ per each predetermined frequency of the frequencies $F_1$ to $F_n$ in the transmitted location signals TR may for example include the following per each predetermined frequency $F_i$:

identifying a pair of packets of the packets PC1 and PC2 received from the first and second acquisition devices 110 and 120, in which both the packets of the pair include at least a portion of the CW calibration signal CS whose frequency is predetermined frequency $F_i$;

Then, processing the pair of packets with that predetermined frequency $F_i$ utilizing spectral processing, such as Goertzel process, to determine the respective amplitudes $A1_i$ and $A2_i$ of that predetermined frequency $F_i$ in the respective packets the pair, which are obtained from the first and second acquisition devices 110 and 120 respectively.

The gain difference $\Delta G_i$ for that predetermined frequency $F_i$ may than be determined based on the ratio between the amplitudes $A1_i$ and $A2_i$ of that predetermined frequency $F_i$ in the calibration signal sampled by the first and second acquisition devices 110 and 120, as follows: $\Delta G_i = A1_i / A2_i$.

Accordingly, the gain differences $\{\Delta G_i\}$ are determined per each of the predetermined frequencies $F_1$ to $F_n$.

In view of the above, method/operation 250, provides for determining synchronization parameters SP for synchronizing between the signals sampled by the first and second signal acquisition devices, 110 and 120. The synchronization parameters SP may include the temporal-misalignment/clock-skew Δt between the first and second acquisition devices 110 and 120, which may be determined in some embodiments with sub-packet resolution, and/or with higher resolution (e.g. by further implementing the optional operation 255-256). In some embodiments the synchronization parameters SP also include data indicative of the gain difference(s) $\{\Delta G_i\}$ between the first and second acquisition devices 110 and 120. As indicated above, in some implementations the differences $\{\Delta G_i\}$ in gains introduced to different frequencies of the predetermined location signals' frequencies $F_1$ to $F_n$ are asserted to be substantially similar, and a single gain difference ΔG is determined in 258 (e.g. based on the comparison of the amplitudes of one frequency component between the calibration signals sampled by the acquisition devices 110 and 120). Alternatively, in some embodiments the gain differences $\{\Delta G_i\}$ are determined per each respective frequency of the predetermined location signals' frequencies $F_1$ to $F_n$.

With reference back together to FIGS. 3 and 4A, the synchronization parameters SP determined by operation 250 are provided to the synchronizer 160, which utilizes them to synchronize between the location signals $RS_1$ and $RS_2$, which were sampled and packed by the first and second acquisition devices 110 and 120 respectively. In this regard, it should be understood that the synchronization parameters SP are typically not determined per each pair of concurrent packets of the location signals obtained via channels CH1 and CH3, but may be determine only once during a medical procedure (e.g. on initialization of the positioning system 100), or determined from time to time during the operation of the positioning system, e.g. at predetermined time intervals, in order to reassess the synchronization parameters SP and compensates for drifts which might occur in the rates of clocks CLK1 and CLK 2, or to compensate for variations in the power inputs to the first and second acquisition devices 110 and 120, which might affect the gain differences between them. For instance, in some implementations the calibration signal generator 134 may be configured to generate the calibration signal CS, which is fed to channels CH2 and CH4, only at certain time intervals; and the synchronization processor 150 may be adapted to carry out operation 250 to determine/update the synchronization parameters SP, only at times there exists a concurrent pair of packet in the packets PC1 and PC2, which include the calibration signal sampled by the first and second acquisition devices 110 and 120 respectively.

In turn, the synchronizer 160 obtains the synchronization parameters SP from the synchronization processor 150 each time they are determined/updated by the synchronization processor 150. The synchronizer 160 carries out the operation 260 and utilizes the synchronization parameters SP to synchronize between the signals the position signals $RS_1$ and $RS_2$ that are acquired by the different, first and second, acquisition devices 110 and 120, and accordingly outputs the synchronized position signals SS being synchronized according to said parameters. The synchronization 260 is generally/typically performed for all the samples of the signals sampled from the first and third channels, CH1 and CH3 based on the updated synchronization parameters SP associated therewith. The synchronization 260 includes synchronizing the timings of the signals sampled from the first and third channels based on the sub-packet resolution time-shift/clock-skew $\Delta t \approx \Delta t_P$ determined in 250. This may for example include shifting the samples sampled from at least one of first and third channels CH3 and CH4 by a number of samples that is equivalent, considering the sampling rate, to the time shift Δt. Optionally, the synchronization 260 synchronizes the timings of the signals sampled from the first and third channels based on the total temporal-misalignment/clock-skew $\Delta t = \Delta t_P + \Delta t_S$ as may be determined in 250 with resolution that is equal to, or approaching, the sampling resolution (e.g. by implementations of operations 251 to 256 of the method 250 illustrated in FIG. 4B). Optionally the synchronization operation 260 also includes operations designated to compensate for any gain difference(s) $\{\Delta G_i\}$ between the first and second acquisition devices 110 and 120, as may be determined in 250 (e.g. by sub operation 258 thereof). This may include adjusting the amplitudes of the position signals $RS_1$ and $RS_2$ or samples thereof, that were sampled by the first and second acquisition devices 110 and 120 (from over the first and third channels CH1 and CH3 thereof) by a factor corresponding-to or equal-to the gain difference ΔG. Optionally, where gain differences are determined per each predetermined frequency (e.g. as described above with reference to 258, the synchronization 260 may include amplitude adjustment performed per each frequency component $F_i$ of the signals $RS_1$ and $RS_2$ according to the respective gain difference $\Delta G_i$ associated therewith. As will be readily appreciated by those versed in the art, the synchronization operation(s) 260, may be performed utilizing for example spectral processing of the position signals $RS_1$ and/or $RS_2$ (e.g. utilizing Goertzel process based on the predetermined frequencies), to identify their phases and/or amplitudes, and adjusting their phases and/or amplitudes according to the synchronization petameters SP. In some implementations the phases and/or amplitudes of the position signals obtained from only one of the acquisition devices (e.g. of signals $RS_2$ obtained from acquisition device 120) are synchronized to match those of the position signals of the acquisition device(s) (e.g. to match the signals $RS_2$ obtained from acquisition device 110). Accordingly in the synchronized position signals SS are indicative of the accurate positions, and in particularly the relative positions, of the position sensors 34.1 and 34.2, which are processed by the first and second acquisition devices 110 and 120 (e.g. of the PIU and AIU) respectively, and thus the relative positions between the medical instruments 26 associated therewith can be determined accurately.

In operation 290 of method 200, the respective positions of the medical instruments 26 of the medical devices 14A and 14B, or of the position sensors 34.1 and 34.2 associated therewith, may be determined, e.g. by positioning utility 190, based on the synchronized position signals obtained from operation 260. As will be readily appreciated by those versed in the art, the position determination itself relative to the respective positions of the signal transmitters, e.g. 32, may be implemented by various known in the art techniques (as long as the phases, and optionally also the amplitudes of the location signals are correctly measured relative to the corresponding transmission signals). This in a non-limiting example may be performed utilizing time-of-arrival (TOA), difference-time-of-arrival (DTOA), triangulation, and or any other suitable techniques or combinations thereof to determine the location(s) and/or the orientation(s) the medical module(s) relative to a reference frame (coordinates) defined by the signal transmitters e.g. 32. Accordingly, the positions of the medical devices 14A and 14B and/or of distal end portions 35 thereof and/or medical instruments 26 thereon can be accurately determined based on the synchronized signals SS by the system 100.

In this regard it should be noted that the respective positions of the medical instruments 26 or devices 14 may be inferred for example based on measurements of the positions of position sensors 34 associated therewith, which may be for example magnetic/electromagnetic based position sensors. Alternatively or additionally, the positions of one or more distal end portions 35 of the medical devices 14, such as the position of a main body (e.g. a catheter's shaft) 29 of a medical device 14 such as catheter 14A or 14B, and/or the position one or more flexible/movable sections/splines 22 thereof, may be determined based on the positions of a plurality of positions sensors. For instance, in some embodiments the position sensors 34.1 or some of them may be arranged near respective medical instruments 26 of the medical device/catheter 14A may not be located with specific proximity to any specific position sensor. The positioning utility 190 may utilize the signals from a combination of the position sensors 34.1 of the medical device 14A, to determine/assess the shape(s) of the distal end flexible/movable sections 22 of the medical-device 14A (e.g. utilizing predetermined data indicative of the flexing behavior of these movable sections 22), to determine, based on the positions of the position sensors 34.1 the flexed/shifted shape of the distal end 28 of the medical-device/catheter 14A and thereby also the positions of the medical instruments 26 that are located thereon. Moreover, in some embodiments the position sensors 34.1 of a medical device such as 14A, may include at least one "main" position sensor 34A which may be located at a certain distal end portion of the medical device 14A, such as for instance its body/shaft 29, and one or more additional position sensors, e.g. 34B to 34K, which may be for instance located on the flexible/movable sections 22 of the medical-device 14A. The "main" position sensor(s) 34A may be implemented as a three axes sensor (TAS) (e.g. including three magnetic coils) capable of sensing the three-dimensional (3D) location and orientation of the certain distal end portion of the medical device 14A, such as the location of its main body/shaft 29; and the one or more additional position sensors, e.g. 34B to 34K, may be implemented as single-axis sensor (SAS) (e.g. each including one magnetic coil capable of sensing their orientation). In such embodiments the positioning utility 190 may be adapted to combine the position signals obtained from one or more of the additional position sensors (e.g. 34B to 34K which may be SAS sensors) with the position signals obtained from the main/TAS position sensor 34A of the medical device 14A in order to determine the 3D locations and/or orientations of the one or more SAS sensors (e.g. based on their self-measured respective orientations, the 3D position of the TAS sensors, and optionally the geometric properties/shape of the medical device 14A while optionally considering its deformation which may be assessed based on the relative orientations of the TAS and SAS position sensors of the medical device).

EXAMPLES

Example 1. A position sensing system 100 including:
a. a calibration signal generator 134 configured to generate a calibration signal CS in the form of a continuous wave (CW) whose frequency is switched between a plurality of frequencies;
b. a first signal acquisition device 110 configured to sample output from a first position sensor 34.1 over a first channel CH1 and the calibration signal CS output from the calibration signal generator 134 over a second channel CH2 and to transmit the sampled output from each of the first and second channels in packets PC1;
c. a second signal acquisition device 120 configured to sample output from a second position sensor 34.2 over a third channel CH3 and the calibration signal CS output from the calibration signal generator 134 over a fourth channel CH4 and to transmit the sampled output from each of the third and fourth channels in packets PC2;
d. a synchronization processor 150 configured to:
   i. identify a pair of concurrent packets of the second and fourth channels CH2 and CH4, including transitions between at least first and second frequencies of the plurality of frequencies;
   ii. determine respective transition times between the first and second frequencies in the sampled outputs of the second and fourth channels CH2 and CH4;
   iii. determine a time shift between the sampling of the outputs performed by the first and second signal acquisition devices 110 and 120, with sub-packet resolution, based on a difference between the respective transition times;
e. a synchronizer 160 adapted to synchronize the outputs of the first and third channels CH1 and CH3, which are associated with the first and second position sensors 34.1 and 34.2, based on the time shift; and
f. a positioning utility 190 adapted to process the synchronized outputs of the first and third channels CH1 and CH3 to determine the positions of the first and second position sensors 34.1 and 34.2, and stream data indicative of the positions to a display 27.

Example 2. The system 100 according to Example 1, wherein determining the respective transition times between the first and second frequencies in the sampled outputs of the second and fourth channels CH2 and CH4, includes determining respective ratios between powers of the first and second frequencies in the concurrent packets respectively.

Example 3. The system 100 according to Example 2, including determining the powers of the first and second frequencies in the concurrent packets by applying spectral processing to the sampled outputs of the second and fourth channels CH2 and CH4 appearing respectively in the concurrent packets.

Example 4. The system 100 according to Example 3, wherein the spectral processing is implemented based on data indicative of the first and second frequencies utilizing a Goertzel process.

Example 5. The system 100 according to any one of Examples 1 to 4, wherein the first and second signal acquisition devices 110 and 120 introduce different amplitude gains to sampled outputs of the first and second channels (CH1, CH2) and to the third and fourth channels (CH3, CH4), that are respectively sampled thereby; and wherein the synchronization processor is further configured to compare amplitudes of the sampled outputs of the second and fourth channels CH2 and CH4 to determine gain-difference between the amplitude gains introduced to the sampled outputs of the first and third channels CH1 and CH3 by the first and second signal acquisition devices 110 and 120 respectively; the synchronizer 160 is further configured to apply gain compensation to adjust the amplitudes of signal components in the output of at least one of the first and third channels CH1 and CH3 to compensate for the gain-difference, thereby obtaining the synchronized sampled outputs of the first and third channels CH1 and CH3 as gain-compensated outputs; and the positioning utility 190 is adapted to process the gain-compensated outputs from the first and third channels CH1 and CH3 to accurately determine the positions of the first and second position sensors 34.1 and 34.2, based on the adjusted amplitudes.

Example 6. The system 100 according to Example 5, wherein the amplitude gains may be different for different frequencies; wherein the calibration signal generator generates the continuous wave (CW) such that the plurality of frequencies include a plurality of predetermined frequencies $F_1$ to $F_n$ that are expected to be received from the first and second position sensors 34.1 and 34.2 over the first and third channels CH1 and CH3, and switches between the plurality of frequencies $F_1$ to $F_n$ with time intervals between frequency switches that is longer than a time duration of the packets containing the outputs of the second and fourth channels CH2 and CH4. The synchronization processor 150 is adapted to identify respective pairs of packets of the second and fourth channels CH2 and CH4 such that both packets in each respective pair include at least one of said predetermined frequencies $F_1$ to $F_n$, and determine gain-differences for the predetermined frequencies $F_1$ to $F_n$ based on amplitudes of each predetermined frequency in the corresponding pair of packets; and the synchronizer carries out the gain compensation per each predetermined frequency of the predetermined frequencies $F_1$ to $F_n$.

Example 7. The system 100 according to any one of Examples 1 to 6, wherein the first and second signal acquisition devices 110 and 120 utilize respective first and second sampling clocks CLK1 and CLK2 to sample the outputs of their associated channels with a sampling resolution; and wherein the first and second sampling clocks CLK1 and CLK2 are not timely aligned thereby introducing a clock skew between the sampled outputs of the first and second channels CH1 and CH2, and the sampled outputs of the third and fourth channels CH3 and CH4. The synchronization processor 150 is further configured to:

process at least one pair of concurrent packets of the outputs of the second and fourth channels CH2 and CH4 that are respectively sampled by the first and second signal acquisition devices 110 and 120, to determine respective phases of a frequency component included in the outputs of both the second and fourth channels CH2 and CH4; and determine the clock skew based on a difference between the respective phases and the time shift; and the synchronizer 160 is further adapted to synchronize the timings of the outputs of the first and third channels CH1 and CH3, to compensate for the clock skew between the first and second signal acquisition devices 110 and 120.

Example 8. The system 100 according to any one of Examples 1 to 7 further including a rate-controller 121 that is adapted to adjust a rate of a sampling clock (e.g. CLK2) of one of the first and second signal acquisition devices 110 and 120 to match a rate of a sampling clock (e.g. CLK1) of the other one of the first and second signal acquisition devices 110 and 120.

Example 9. The system 100 according any one of Examples 1 to 7 further including a rate-controller 141 that is adapted to adjust a sampling rate of signals sampled by at least one of the first and second signal acquisition devices 110 and 120 to match rates of samples in the signals sampled by the first and second signal acquisition devices 110 and 120, and thereby compensate for different clock rates of sampling clocks CLK2 and CLK2 of the first and second signal acquisition devices 110 and 120.

Example 10. A catheter-based mapping and ablation system 10 comprising the positioning system 10 according to any one of Examples 1 to 9.

Example 11. A method 200 of position sensing including:

210—generating a calibration signal CS in the form of a continuous wave (CW) whose frequency is switched between a plurality of frequencies;

220—by a first signal acquisition device 110: sampling an output from a first position sensor 34.1 over a first channel CH1 and the calibration signal CS output over a second channel CH2; and transmitting the sampled outputs of each of the first and second channels CH1 and CH2 in first packets PC1;

230—by a second signal acquisition device 120: sampling an output from a second position sensor 34.2 over a third channel CH3 and the calibration signal output CS over a fourth channel CH4; and transmitting the sampled output from each of the third and fourth channels CH3 and CH4 in second packets PC2;

250—determining synchronization parameters for synchronizing between the signals sampled from each of the first and third channels CH1 and CH3 based on the calibration signal CS sampled from each of the second and forth channels CH2 and CH4; whereby determining of the synchronization parameters includes:

251—identifying a pair of concurrent packets including sampled outputs of the second and fourth channels CH2 and CH4, and in which there are respective transitions between at least first and second frequencies of the plurality of frequencies;

252—determining respective transition times between the first and second frequencies in the sampled outputs of the second and fourth channels CH2 and CH4; and

253—determining a time shift between the sampling of the outputs performed by the first and second signal acquisition devices 110 and 120, with sub-packet resolution, based on a difference between said respective transition times; and

260—synchronizing the outputs of the first and third channels CH1 and CH3, which are associated with the first and second position sensors 34.1 and 34.2, based on the time shift; and

290—streaming, to a display 27, data indicative of positions of the first and second position sensors 34.1 and 34.2, determined based on the synchronized outputs of the first and third channels CH1 and CH3.

Example 12. The method 200 according to Example 11 wherein determining the respective transition times between the first and second frequencies in the sampled outputs of the second and fourth channels CH2 and CH4 includes determining respective ratios between powers of the first and second frequencies in the concurrent packets PC1 and PC2 respectively.

Example 13. The method 200 according to Example 12, further includes determining the powers of the first and second frequencies in the concurrent packets by applying spectral processing to the sampled outputs of the second and fourth channels CH2 and CH4 appearing respectively in the concurrent packets.

Example 14. The method 200 according to Example 13 wherein the spectral processing is implemented utilizing a Goertzel process based on data indicative of the first and second frequencies.

Example 15. The method 200 according to any one of Examples 11 to 14, wherein the first and second signal acquisition devices 110 and 120, introduce different amplitude gains to sampled outputs of the first and second channels CH1 and CH2 and to sampled outputs of the third and fourth channels CH3 and CH4, which are respectively sampled thereby; and wherein the determining (250) of the synchronization parameters further includes comparing amplitudes of the sampled outputs of the second and fourth channels CH2 and CH4 to determine 258 gain-difference between the amplitude gains introduced to the sampled outputs of the first and third channels CH1 and CH3 by the first and second signal acquisition devices 110 and 120. The synchronizing (260) of the sampled outputs further includes carrying out gain compensation to adjust the amplitudes of signal components in the output of at least one of the first and third channels CH1 and CH3 to compensate for the gain-difference and thereby obtain the synchronized outputs of the first and third channels CH1 and CH3 as gain-compensated outputs. the positions of the first and second position sensors 34.1 and 34.2 are determined by processing the gain-compensated outputs of the first and third channels CH1 and CH3.

Example 16. The method 200 according to Example 15, wherein the amplitude gains may be different for different frequencies. The plurality of frequencies of the calibration signal CS include a plurality of predetermined frequencies $F_1$ to $F_n$ that are expected to be received from the first and second position sensors 34.1 and 34.2 over the first and third channels CH1 and CH3, and the method 200 includes switching the frequency of the calibration signal CS, between the plurality of frequencies $F_1$ to $F_n$, with time interval of the switching that is longer than a time duration of the packets containing the outputs of the second and fourth channels CH2 and CH4. The determining (250) of the synchronization parameters includes the following, per each predetermined frequency of the plurality of predetermined frequencies $F_1$ to $F_n$:

identifying respective pairs of packets with the second and fourth channels CH2 and CH4 including the predetermined frequency, and determine gain-difference per each predetermined frequency based on amplitudes of the predetermined frequency in a corresponding pair of packets of the respective pairs;

The synchronizing (260) further includes carrying out gain compensation per each predetermined frequency.

Example 17. The method 200 according to any one of Examples 11 to 16 wherein the first and second signal acquisition devices 110 and 120 utilize respective first and second sampling clocks CLK1 and CLK2 to sample the outputs of their associated channels with a sampling resolution; and wherein the first and second sampling clocks CLK1 and CLK2 are not timely aligned thereby introducing a clock skew between the sampled outputs of said first and second channels CH1 and CH2, and the sampled outputs of the third and fourth channels CH3 and CH4; and wherein the determining (250) of the synchronization parameters further includes:

255—processing at least one pair of concurrent packets of the outputs of the second and fourth channels CH2 and CH4 that are respectively sampled by the first and second signal acquisition devices 110 and 120, to determine respective phases of at least one frequency included in the outputs of both the second and fourth channels CH2 and CH4; and

256—determining the clock skew based on a difference between the respective phases; and the synchronizing (260) further includes synchronizing outputs of the first and third channels CH1 and CH3 to compensate for the clock skew.

Example 18. The method 200 according to any one of Examples 11 to 17 including adjusting a rate of a sampling clock (e.g. CLK2) of one of the first and second signal acquisition devices 110 and 120 to match a rate of a sampling clock (e.g. CLK1) of the other one of the first and second signal acquisition devices 110 and 120.

Example 19. The method 200 according to any one of Examples 11 to 17 including interpolating the signals sampled by at least one of the first and second signal acquisition devices 110 and 120 to adjust their sampling rates such that rates of samples in the signals sampled by the first and second signal acquisition devices 110 and 120 are matching, thereby compensating for different clock rates in sampling clocks CLK1 and CLK2 of the first and second signal acquisition devices 110 and 120.

It should also be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof, which would occur to persons of ordinary skills in the art upon reading the description of the present invention and which are not disclosed in the prior art.

The invention claimed is:

1. A position sensing system comprising:

a. a calibration signal generator configured to generate a calibration signal in the form of a continuous wave (CW) whose frequency is switched between a plurality of frequencies;

b. a first signal acquisition device configured to sample output from a first position sensor over a first channel and the calibration signal output from said calibration signal generator over a second channel and to transmit the sampled output from each of said first and second channels in packets;

c. a second signal acquisition device configured to sample output from a second position sensor over a third channel and the calibration signal output from said calibration signal generator over a fourth channel and to transmit the sampled output from each of said third and fourth channels in packets;

d. a synchronization processor configured to:

i. identify a pair of concurrent packets of said second and fourth channels including transitions between at least first and second frequencies of said plurality of frequencies;

ii. determine respective transition times between the first and second frequencies in the sampled outputs of said second and fourth channels;

iii. determine a time shift between the sampling of the outputs performed by said first and second signal acquisition devices, with sub-packet resolution, based on a difference between said respective transition times;

e. a synchronizer adapted to synchronize the outputs of said first and third channels, which are associated with the first and second position sensors, based on said time shift; and f. a positioning utility adapted to process the synchronized outputs of said first and third channels to determine the positions of said first and second position sensors, and stream said data indicative of said positions to a display.

2. The system according to claim 1 wherein determining the respective transition times between said first and second frequencies in the sampled outputs of said second and fourth channels comprises determining respective ratios between powers of the first and second frequencies in said concurrent packets respectively.

3. The system according to claim 2 comprising determining said powers of the first and second frequencies in said concurrent packets by applying spectral processing to the sampled outputs of the second and fourth channels appearing respectively in said concurrent packets.

4. The system of according to claim 3 wherein the spectral processing is implemented based on data indicative of said first and second frequencies utilizing a Goertzel process.

5. The system according to claim 1, wherein said first and second signal acquisition devices introduce different amplitude gains to sampled outputs of the first and second channels and to the third and fourth channels, that are respectively sampled thereby; and wherein the synchronization processor is further configured to compare amplitudes of the sampled outputs of the second and fourth channels to determine gain-difference between the amplitude gains introduced to the sampled outputs of the first and third channels by said first and second signal acquisition devices respectively; the synchronizer is further configured to apply gain compensation to adjust the amplitudes of signal components in the output of at least one of said first and third channels to compensate for said gain-difference, thereby obtaining said synchronized sampled outputs of said first and third channels as gain-compensated outputs; and said positioning utility is adapted to process the gain-compensated outputs from said first and third channels to accurately determine said positions of the first and second position sensors, based on the adjusted amplitudes.

6. The system according to claim 5, wherein said amplitude gains may be different for different frequencies; wherein said calibration signal generator generates said continuous wave (CW) such that said plurality of frequencies comprise a plurality of predetermined frequencies expected to be received from the first and second position sensors over said first and third channels, and switches between said plurality of frequencies with time intervals between frequency switches that is longer than a time duration of the packets containing the outputs of said second and fourth channels; wherein said synchronization processor is adapted to identify respective pairs of packets of said second and fourth channels, such that both packets in each respective pair include at least one of said predetermined frequencies, and determine gain-differences for said predetermined frequencies based on amplitudes of each predetermined frequency in the corresponding pair of packets; and said synchronizer carries out the gain compensation per each predetermined frequency of said predetermined frequencies.

7. The system according to claim 1, wherein said first and second signal acquisition devices utilize respective first and second sampling clocks to sample the outputs of their associated channels with a sampling resolution; and wherein the first and second sampling clocks are not timely aligned thereby introducing a clock skew between the sampled outputs of said first and second channels, and the sampled outputs of the third and fourth channels; and wherein the synchronization processor is further configured to:

process at least one pair of concurrent packets of the outputs of said second and fourth channels that are respectively sampled by said first and second signal acquisition devices, to determine respective phases of a frequency component included in the outputs of both said second and fourth channels; and determine said clock skew based on a difference between said respective phases and said time shift; and said synchronizer is further adapted to synchronize the timings of the outputs of said first and third channels, to compensate for said clock skew between the first and second signal acquisition devices.

8. The system according to claim 1 further comprising a rate-controller that is adapted to adjust a rate of a sampling clock of one of said first and second signal acquisition devices to match a rate of a sampling clock of the other one of said first and second signal acquisition devices.

9. The system according to claim 1 further comprising a rate-controller that is adapted to adjust a sampling rate of signals sampled by at least one of said first and second signal acquisition devices to match rates of samples in the signals sampled by said first and second signal acquisition devices, and thereby compensate for different clock rates of sampling clocks of said first and second signal acquisition devices.

10. A catheter-based mapping and ablation system comprising the positioning system according to claim 1.

11. A method of position sensing comprising:

a. generating a calibration signal in the form of a continuous wave (CW) whose frequency is switched between a plurality of frequencies;

b. by a first signal acquisition device: sampling an output from a first position sensor over a first channel and the calibration signal output from said calibration signal generator over a second channel; and transmitting the sampled outputs of each of the first and second channels in first packets;

c. by a second signal acquisition device: sampling an output from a second position sensor over a third channel and the calibration signal output from said calibration signal generator over a fourth channel; and transmitting the sampled output from each of said third and fourth channels in second packets;

d. determining synchronization parameters for synchronizing between the signals sampled from each of said first and third channels based on the calibration signals sampled from each of the second and forth channels; whereby said determining of the synchronization parameters comprises:

i. identifying a pair of concurrent packets including sampled outputs of said second and fourth channels, and in which there are respective transitions between at least first and second frequencies of said plurality of frequencies;

ii. determining respective transition times between the first and second frequencies in the sampled outputs of said second and fourth channels; and iii. determining a time shift between the sampling of the outputs performed by said first and second signal acquisition devices, with sub-packet resolution, based on a difference between said respective transition times; and e. synchronizing the outputs of said first and third channels, which are associated with the first and second position sensors, based on said time shift; and f. streaming, to a display, data indicative of concurrent positions of the first and second position sensors, determined based on the synchronized outputs of said first and third channels.

12. The method according to claim 11 wherein determining the respective transition times between said first and second frequencies in the sampled outputs of said second and fourth channels comprises determining respective ratios between powers of the first and second frequencies in said concurrent packets respectively.

13. The method according to claim 12 comprising determining said powers of the first and second frequencies in said concurrent packets by applying spectral processing to the sampled outputs of the second and fourth channels appearing respectively in said concurrent packets.

14. The method according to claim 13 wherein the spectral processing is implemented utilizing a Goertzel process based on data indicative of said first and second frequencies.

15. The method according to claim 11, wherein said first and second signal acquisition devices introduce different amplitude gains to sampled outputs of the first and second channels and to sampled outputs of the third and fourth channels, which are respectively sampled thereby; and wherein said determining of the synchronization parameters further comprises comparing amplitudes of the sampled outputs of the second and fourth channels to determine gain-difference between the amplitude gains introduced to the sampled outputs of the first and third channels by said first and second signal acquisition devices; and said synchronizing of the sampled outputs further comprises carrying out gain compensation to adjust the amplitudes of signal components in the output of at least one of said first and third channels to compensate for said gain-difference and thereby obtain said synchronized outputs of the first and third channels as gain-compensated outputs; and wherein the positions of the first and second position sensors are determined by processing the gain-compensated outputs of said first and third channels.

16. The method according to claim 15, wherein said amplitude gains may be different for different frequencies; wherein said plurality of frequencies of the calibration signal comprise a plurality of predetermined frequencies that are expected to be received from the first and second position sensors over said first and third channels, and the method includes switching the frequency of the calibration signal, between said plurality of frequencies, with time interval of said switching that is longer than a time duration of the packets containing the outputs of said second and fourth channels; and wherein said determining of the synchronization parameters comprises the following, per each predetermined frequency of said plurality of predetermined frequencies: identifying respective pairs of packets with said second and fourth channels including said predetermined frequency, and determine gain-difference per each predetermined frequency based on amplitudes of the predetermined frequency in a corresponding pair of packets of said respective pairs; and wherein said synchronizing further includes carrying out said gain compensation per each said predetermined frequency.

17. The method according to claim 11, wherein said first and second signal acquisition devices utilize respective first and second sampling clocks to sample the outputs of their associated channels with a sampling resolution; and wherein the first and second sampling clocks are not timely aligned thereby introducing a clock skew between the sampled outputs of said first and second channels, and the sampled outputs of the third and fourth channels; and wherein said determining of the synchronization parameters further comprises: processing at least one pair of concurrent packets of the outputs of said second and fourth channels that are respectively sampled by said first and second signal acquisition devices, to determine respective phases of at least one frequency included in the outputs of both said second and fourth channels; and determining said clock skew based on a difference between said respective phases; and said synchronizing further comprises synchronizing outputs of said first and third channels to compensate for said clock skew.

18. The method according to claim 11 comprising adjusting a rate of a sampling clock of one of said first and second signal acquisition devices to match a rate of a sampling clock of the other one of said first and second signal acquisition devices.

19. The method according to claim 11 comprising interpolating the signals sampled by at least one of said first and second signal acquisition devices to adjust their sampling rates such that rates of samples in the signals sampled by said first and second signal acquisition devices are matching, thereby compensating for different clock rates in sampling clocks of said first and second signal acquisition devices.

\* \* \* \* \*